United States Patent [19]
Perez-Soler et al.

[11] Patent Number: 5,834,012
[45] Date of Patent: Nov. 10, 1998

[54] LIPID COMPLEXED TOPOISOMERASE I INHIBITORS

[75] Inventors: Roman Perez-Soler, 2904 Rice Blvd., Houston, Tex. 77005; Steven M. Sugarman, 7 Baron Ct., Stony Brook, N.Y. 11790; Kenneth R. Poirot, 8450 Cambridge St., Apt. 2213, Houston, Tex. 77054

[73] Assignees: Roman Perez-Soler; Steven M. Sugarman; Kenneth R. Poirot, all of Houston, Tex.

[21] Appl. No.: 433,289

[22] Filed: May 3, 1995

[51] Int. Cl.$^6$ ............................................. A61K 9/127
[52] U.S. Cl. ............................................. 424/450
[58] Field of Search ............................................. 424/450

[56] References Cited

U.S. PATENT DOCUMENTS

| | | | |
|---|---|---|---|
| 3,993,754 | 11/1976 | Rahman et al. | 424/450 |
| 4,863,739 | 9/1989 | Perez-Soler et al. | 424/450 |
| 4,906,477 | 3/1990 | Kurono et al. | 424/450 |
| 5,498,421 | 3/1996 | Grinstaff et al. | 424/450 |
| 5,527,528 | 6/1996 | Allen et al. | 424/450 |

OTHER PUBLICATIONS

Burke et al., "Liposomal Stabilization of Camptothecin's Lactone Ring," *J. Am. Chemical Soc.*, 114:8318–8319, 1992.

Fraley et al., "Introduction of Liposome–encapsulated SV40 DNA into Cells," *The Journal of Biological Chemistry*, 255(21):10431–10435, 1980.

Giovanella et al., "DNA Topoisomerase I–Targeted Chemotherapy of Human Colon Cancer in Xenografts," *Science*, 246:1046–1048, Nov. 1989.

Giovanella et al., "Complete Growth Inhibition of Human Cancer Xenografts in Nude Mice by Treatment with 20–(S)–Camptothecin," *Cancer Research*, 51:3052–3055, Jun. 1991.

Gottlieb et al., "Preliminary Pharmacologic and Clinical Evaluation of Camptothecin Sodium (NSC–100880)," *Cancer Chemotherapy Reports Part 1*, 54(6):461–470, Dec. 1970.

Hart et al., "A Fluorometric Method for Determination of Camptothecin in Plasma and Urine," *Cancer Chemotherapy Reports Part 1*, 53(4):211–214, Sep. 1969.

Hertzberg et al., "Modification of the Hydroxy Lactone Ring of Camptothecin: Inhibition of Mammalian Topoisomerase I and Biological Activity," *Journal of Medicinal Chemistry*, 32(3):715–720, 1989.

Hsiang et al., "Camptothecin Induces Protein–linked DNA Breaks via Mammalian DNA Topoisomerase I," *The Journal of Biological Chemistry*, 260(27):14873–14878, Nov. 25, 1985.

Hsiang and Liu, "Identification of Mammalian DNA Topoisomerase I as an Intracellular Target of the Anticancer Drug Camptothecin," *Cancer Research*, 48:1722–1726, Apr. 1, 1988.

Kaplan and Meier, "Nonparametric Estimation from Incomplete Observations," *American Statistical Association Journal*, 457–481, Jun. 1958.

Kohn et al., "Cell Cycle Control and Cancer Chemotherapy," *Journal of Cellular Biochemistry*, 54:440–452, 1994.

Mattern et al., "Relationship between the Intracellular Effects of Camptothecin and the Inhibition of DNA Topoisomerase I in Cultured L1210 Cells," *Cancer Research*, 47:1793–1798, Apr. 1987.

(List continued on next page.)

*Primary Examiner*—Peter F. Kulkosky
*Attorney, Agent, or Firm*—Arnold, White & Durkee

[57] ABSTRACT

The present invention is described as a lipid-complexed topoisomerase I inhibitor (TII), for example camptothecin (CPT) preparation that allows for intravenous administration in vivo in clinically relevant lipid:drug ratios. The lipid formulation has in vitro antitumor activity similar to that of the base compound and displays similar cytotoxicity against both MDR-1 negative and positive tumor cells.

29 Claims, 13 Drawing Sheets

OTHER PUBLICATIONS

Moertel et al., "Phase II Study of Camptothecin (NSC–100880) in the Treatment of Advanced Gastrointestinal Cancer," *Cancer Chemotherapy Reports Part I,* 56(1):95–101, Feb. 1972.

Muggia et al., "Phase I Clinical Trial of Weekly and Daily Treatment With Camptothecin (NSC–100880): Correlation With Preclinical Studies," *Cancer Chemotherapy Reports Part I,* 56(4):515–523, Aug. 1972.

Slichenmyer et al., "The Current Status of Camptothecin Analogues as Antitumor Agents," *Journal of the National Cancer Institute,* 85(4):271–291, Feb. 1993.

Stamatatos etal., "Interactions of Cationic Lipid Vesicles with Negatively Charged Phospholipid Vesicles and Biological Membranes," *Biochemistry,* 27:3917–3925, 1988.

Wall et al., "Plant Antitumor Agents. I. The Isolation and Structure of Camptothecin, a Novel Alkaloidal Leukemia and Tumor inhibitor from *Camptotheca acuminata,"* *Journal of the American Chemical Society,* 88(16):3888–3890, Aug. 1966.

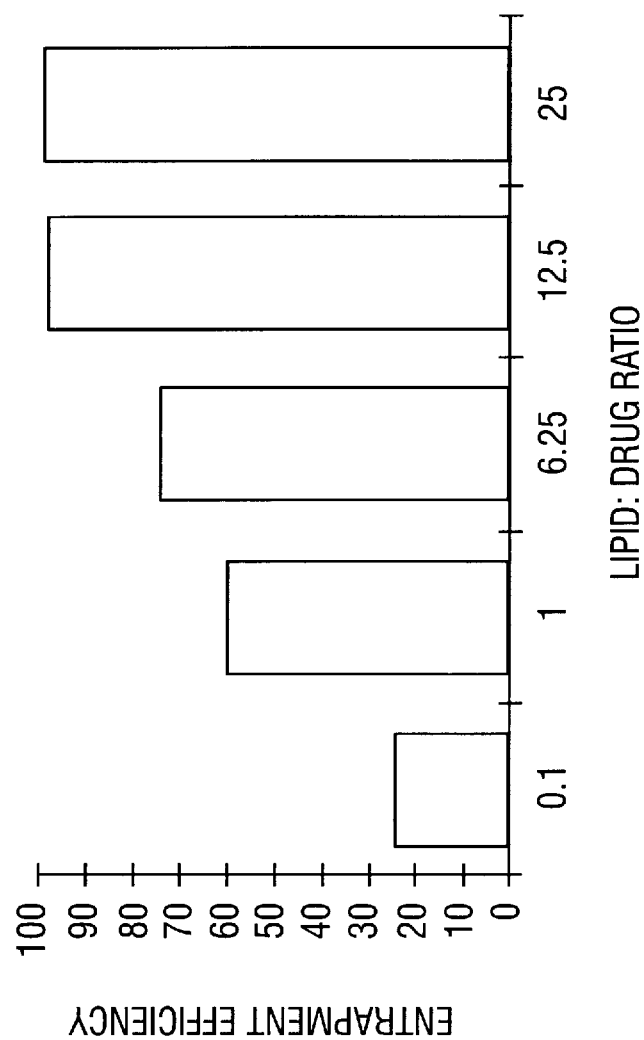

LIPID COMPLEXED TOPOISOMERASE I INHIBITORS

BACKGROUND OF THE INVENTION

1. Field of the Invention

The present invention relates to the production and characterization of the formation of a lipid complexed Topoisomerase I inhibitor (LC-TII) that is easy to prepare and allows for intravenous administration in vivo in clinically relevant lipid:drug ratios. The lipid formulation has in vitro antitumor activity similar to that of camptothecin (CPT) and displays cytotoxicity against multiple drug resistance-1 gene (MDR-1) negative and positive tumor cells, and can be used to kill both MDR-1 negative and positive cells in procedures for deleting populations of cells. The in vivo biodistribution of LC-TII is profoundly affected by lipid complexation. LC-TII of the present invention has significant antitumor activity in vivo against leukemia and is more potent than the free inhibitor.

2. Background of the Related Art

The topoisomerase I inhibitor, Camptothecin (CPT), is a drug isolated from the stemwood of the oriental tree, *Camptotheca Acuminata*, that passed random drug screening tests in the 1950's and was characterized by Wall in 1965 (Wall et al. 1966). Clinical trials using the sodium salt of CPT demonstrated activity in human tumors in the early 1970's, particularly in patients with intestinal tumors metastatic to the liver, but the drug fell out of favor because of dose-limiting leukopenia, cystitis, and gastroenteritis (Gottlieb et al., 1970; Muggia et al., 1972; Moertel et al., 1972).

Interest in CPT was revived when it was found to have a unique mechanism of action: topoisomerase I inhibition (Hsiang et al., 1985; Mattern et al., 1985; Hsiang and Liu, 1988). Inhibition of topoisomerase I causes nicks in single-stranded DNA, resulting in arrest in the G2 phase of the cell cycle (Kohn et al., 1994). G2 arrest is seen with a variety of cytotoxic agents; it appears to result from a failure to activate cdc2 kinase, an enzyme required for chromosome condensation and nuclear membrane breakdown prior to mitosis.

CPT was originally plagued by solubility problems associated with its hydrophobic properties. For the sodium salt of CPT (carboxylate form) is significantly less active than the lipophilic base compound (closed lactone ring) (Hertzberg et al., 1989). Several analogs were developed to enhance water solubility while maintaining the closed lactone ring form. Topotecan, CPT-11, 9-amino camptothecin and 9-nitro camptothecin are examples of analogs that show promise in vivo and are currently being evaluated in phase I and II clinical trials. Collectively, camptothecin and its analogs are known as topoisomerase I inhibitors (TIIs). Slichenmyer provides an excellent summary of the current status of these trials (Slichenmyer et al., 1993). Although response data has not yet matured, preclinical studies suggest that CPT analogs will demonstrate effectiveness in colon, lung, ovarian, and breast cancer (Giovanella et al., 1991).

Significant activity demonstrated by the parent compound and the poor aqueous solubility of the lactone ring closed form of CPT, could suggest the possibility of trapping the TII drugs in artificial, biologic membranes (liposomes) as a method for delivery of this highly lipophilic compound. The complexation of CPT with lipids might have several advantages: (1) the development of a delivery system for in vivo administration. (2) Enhancement of cytotoxicity by providing a slow drug release system since it is a S-phase specific agent. (3) Improvement of tumor targeting by prolonging the plasma circulation time. (4) Protection of the intact lactone ring from hydrolysis in the circulation. However, studies showed that, despite its significant hydrophobicity, CPT is particularly difficult to entrap in lipid membranes.

Because CPT and its hydrosoluble analogs are particularly difficult to entrap in lipid membranes, no clinically relevant formulation for delivering lactone-intact camptothecin analogs has been described. In spite of their lack of solubility in water, these compounds have a low affinity for lipid membranes composed of a wide variety of lipids, and, as a result are incorporated at very low efficiency in lipid bilayers. When entrapment is attempted most of the drug precipitates as free crystals in the aqueous phase. Previously described liposomal formulations of CPT demonstrate a significant protection of the lactone ring, but require very high ratios of lipid to drug to avoid drug crystallization. These ratios are difficult to administer in the clinic, because so much lipid must be given relative to the amount of drug. For example, Burke et al. 1993 report "high" drug concentration to be when the drug to lipid ratio is 1:150. With these prior entrapment methods, camptothecin will not be entrapped in low levels of lipid, but rather precipitate out of the aqueous phase.

The present inventors have developed lipid complexed topoisomerase I inhibitor formulations (LC-TII), e.g., lipid-complexed CPT (LC-CPT), that provides efficient complexing of lipid to the inhibitor and that maintains in vitro and in vivo cytotoxicity comparable to that of the free compound. A key finding of the invention is that lipids with unsaturated fatty acids have a much higher affinity for CPT. This novel formulation is a LC-TII micellar complex with a very high camptothecin entrapment efficiency. The LC-CPT formulation maintains the lactone ring of CPT in its most stable and clinically effective form. Finally, LC-TII has improved biodistribution characteristics that direct the CPT to target organs without the nephritis associated with the use of similar effective doses of TII.

SUMMARY OF THE INVENTION

The present invention concerns lipid complexed topoisomerase I inhibitor (LC-TII) formulations that provide efficient entrapment of a topoisomerase I inhibitor in clinically relevant concentrations and maintain TII cytotoxicity comparable to that of the free active compounds.

The inventors have developed a formulation of LC-TII that demonstrates activity equivalent to that of the free compound against several human tumor cell lines in vitro and has approximately twice the in vivo potency of free TII in the treatment of transformed cells in mice. These complexes allow a lipid: drug ratios an order of magnitude lower than the lipid: drug ratios previously known. The present invention also demonstrates improved biodistribution, improved pharmacokinetics and both in vitro and in vivo antitumor activity for this formulation of LC-TII.

The invention is based in part on two findings of the inventors. First, the inventors have discovered that lipids with unsaturated fatty acids, particularly the fatty acid oleic, have a high affinity for CPT. Further, it has been discovered that positively charged lipids, such as stearylamine and DOTAP enhance lipid complexation and the entrapment of CPT within lipid bilayers.

The present invention concerns lipid/drug complexes comprising an inhibitor of topoisomerase I of the camptothecin class and phospholipids with unsaturated fatty acids. The presence of unsaturated fatty acids appears to be important to achieve a good complexation with camptothecin Family members. The complexes may be micellar particles or liposomes depending on the lipids used. In order to unify the nomenclature the general term micelle will be used to refer to both micelles and inverted micelles. The general term liposome will be used to describe the incorporation of the drug in a spherical (or vesicular) structure (visualized by fluorescent microscopy). The term liposome will be used to describe both unilamellar and multilamellar liposomes.

As used herein the term topoisomerase I inhibitor (TII) refers to those molecules within the camptothecin genus that are able to inhibit topoisomerase I. Camptothecin family members include: camptothecin, 9-aminocamptothecin, 9-nitrocamptothecin, 10-hydroxy camptothecin, topotecan, 9-chloro-10,11-methylenedioxy (20S)-camptothecin (CMC), CPT-11, SN 38 and the like, and as will be known to those of skill in the art. The preferred LC-TII comprise camptothecin, topotecan, CPT-11, 9-aminocamptothecin, and 9-nitrocamptothecin. However, combinations of these compounds also are possible.

The lipid-complexed topoisomerase I inhibitor of the present invention may be described as a complex comprising a lipid component that forms a micellar complex with the topoisomerase-I inhibitor or liposomes incorporating the TII (<0.1 $\mu$m). The liposomal TII of the present invention may be described as spherical lipid vesicles that have a range of diameter up to about one micron that incorporate the TII. The topoisomerase-I inhibitor employed in the complex can be in either the closed lactone ring lipophilic form or the carboxy form of camptothecin or its derivatives. However, for use with the present invention a preponderance of the closed lactone form of camptothecin and its family members is preferred. A preponderance of the closed ring form is used to describe the percentage of camptothecin in the closed lactone ring form, wherein the percentage of about 60 to 100 percent is particularly preferred.

The lipid component of the LC-TII is composed of any number of different lipids (either alone or in combination). Preferred lipids are phospholipids with one or two mono or poly-unsaturated fatty acids, such as oleic (18:1), linoleic (18:2), linoleoleic (18:3), eicosenoic (20:1), myristoleic (14:1), palmitoleic (16:1), etc., and different neutral, positively charged, and negatively charged polar head groups such as choline, ethanolamine, glycerol, or serine, with or without different covalent associated moieties (covalent association phospholipids). For example, the lipid may be: dioleoyl phosphatidylglycerol (DOPG), dioleoyl phosphatidylcholine (DOPC), or dioleoyl phosphatidylserine (DOPS). Cationic lipids, such as phosphatidylethanolamine (DOPE), (DOTMA), dioleoyl 1-3-dioleoyl Trimethylammonium-propane (DOTAP), stearylamine etc. can also be used. Particularly preferred phospholipids contain the fatty acid chain oleic (18:1 -this denotes that the fatty acid chain contains 18 carbons and 1 unsaturated double bond). When oleic acid is covalently bound to a head group, it is termed "oleoyl". The addition of cationic lipids such as DOTAP and stearylamine can be used to enhance lipid complexation with CPT. PEG-phospholipids can be added to prolong the half life of the lipid/drug complexes. Cholesterol can also be incorporated to enhance the stability of the complexes. Further preferred embodiments comprise the covalent associate phospholipids described below.

One contemplated formulation is comprised of CPT and a covalent association phospholipid (CA lipid), i.e., dioleoyl-N-glutaryl-phosphatidyl ethanolamine (DO-NGPE). CA lipids are typically used to covalently associate ligands such as proteins with the exterior surface of liposomes. These lipids have not heretofore been employed as a major structural component of a lipid drug micellar complex. Examples of commercially available covalent association phospholipids are N-PDP-phosphatidylethanolamine, N-succinyl-phosphatidylethanolamine, N-glutaryl-phosphatidylethamolamine, N-dodecanyl-phosphatidylethanolamine and N-biotinyl-phosphatidylethanolamine. NGPE has been found to be a particularly preferred lipid. NGPE has two negative charges, and it is anticipated that other lipids having two negative charges will have advantages similar to NGPE. A CA lipid may be present as the only lipid in an LC-TII, or as one of two or more lipid components of LC-TII. For example, a CA lipid may form from 1%–100% of the lipid portion of an LC-TII. Preferably, the CA lipid will be in the range of 25%–100% of the lipid portion, with all percentages between these points being possible.

Other preferred lipids are those with at least one unsaturated fatty acid such as DOPE, DOPC, DOTAP, DOPG, DOPS, and DOTMA. The unsaturated fatty acid oleic appears particularly preferred. Combinations of such unsaturated fatty acids are also contemplated. For example, two or more such lipids may be used in combination, either alone or in conjunction with other lipid components. The ratio of an individual lipid within a combination may vary. For example, as little as 1% of a certain lipid, or less, may result in certain advantages. However, typically at least 10% of a lipid will be present. Any combination of lipids which exhibits the characteristics of TII complexation as taught by the specification is considered to be within the scope of the invention. Combinations of one or more lipids in concentrations of an individual lipid of between 1% and 99% of total lipid content, with the sum of a lipid equaling 100% of the lipid component of the LC:TII are contemplated. One preferred embodiment employs a combination of DOPE, DOPC, and DOTAP. In the preferred combination of DOPE, DOPC, and DOTAP, 10–80% DOPE, 10–80% DOPC, and 10–80% DOTAP may be used, with the sum of all these percentages, along with any other lipid components, being 100% of the lipid content of the combination. Preferably, 10–60% DOPE, 10–60% DOPC, and 10–60% DOTAP will be employed, where the sum of these percentages, along with the percentage of any other lipid components, is 10–90%. In a presently preferred embodiment, the ratio of 40% DOPE: 40% DOPC: 20% DOTAP is used.

Any ratio of 100:1 to 5:1 lipid:drug, or even 150:1 by weight ratio will have utility. For example, ratios of 100:1, 90:1, 80:1, 70:1, 60:1, 50:1, 40:1, 30:1, 20:1, and 10:1 will be useful. Those complexes comprising a ratio between about 5:1 and 25:1 will be particularly advantageous and are particularly preferred. The inventors have used lipid:drug ratios of 12.5:1.

Another aspect of the invention involves the use of positively charged, cationic, lipids to assist in complexing and maintaining of stability of the TII. For example, it has been shown that cationic lipids such as stearylamine, DOTAP, DOTMA, DODAP, Distearoyl TAP and Distearoyl DAP, are useful in this regard. DOTAP and stearylamine are particularly preferred cationic lipids. A cationic lipid may be present in a concentration of between 1% and 99% of the total lipid content of the LC-TII. Preferably, a cationic lipid may be present in a concentration of between 10% and 90%. Of course, the percentage of the cationic lipid, like all lipids in the LC-TII, may be anywhere between these points i.e., 10%, 20%, 30%, 40%, 50% 60%, 70% or 80% or anywhere in between preferably, the cationic lipid is present at a concentration between 10% and 50%, with 20% being employed in a presently preferred embodiment.

The invention contemplates compositions comprising LC-TII in pharmaceutically acceptable carrier. As used herein, "pharmaceutically acceptable carrier" includes any and all solvents, surfactants sugars, dispersion media, coatings, antibacterial and antifungal agents, isotonic and absorption delaying agents and the like. The phrase "pharmaceutically acceptable" also refers to molecular entities and compositions that do not produce an allergic or similar untoward reaction when administered to a human.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. Aqueous compositions (inocula) for delivery and use with the present invention comprise an effective amount of the LC-TII dissolved or dispersed in a pharmaceutically acceptable aqueous medium. Such compositions are also referred to as inocula.

The preparation of an inocula comprising the micellar composition that contains a member of the camptothecin genus as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

An inocula can also be formulated into an acceptable composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions containing the LC-TII of the present invention will be administered in a manner compatible with the dosage formulation and in such amount as is therapeutically effective. The formulations are easily administered in a variety of dosage forms such as injectable solutions, drug release capsules and the like.

For peritoneal or parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The present invention is particularly useful for the treatment of cells, including transformed cells and tumors. A particularly preferred use for the LC-TII complexes of the present invention is for the inhibition of both in vitro and in vivo topoisomerase activity. Furthermore, when contemplating the site of delivery of the lipid/drug complexes of the present invention, the inventors discovered that the complexes provided for not only improved drug delivery, but also improved biodistribution by reducing the kidney drug levels.

The inventors contemplate that the present invention delivers camptothecin into cells in a more efficient manner. It is proposed that camptothecin can be coupled with lipids and directly administered via a catheter. The efficient delivery of the compositions of the present invention direct drug delivery to specific sites in vivo, not just the liver and spleen cells which are accessible via intravenous intraperitoneal, intraarterial and/or intrapleural injection. Therefore, this invention also encompasses compositions of camptothecin formulated as a camptothecin/lipid complex and methods of using such constructs.

Those of skill in the art will recognize that there are a variety of lipid vesicles that will be useful in the present invention from large multilamellar liposomes at one end of the spectrum to micelles at the other end of the spectrum. All lipid/drug complex forms, LC-TII from micelles to inverted micelles, to multi-or uni-lamellar liposomes, etc. are within the scope of the claims as defined by their components. The inventors have had particular success with micelles comprising DO-NGPE, and with those comprising DOPE, DOPC, and/or DOTAP. The inventors have also had success with micelles comprising DO-NGPE that have been prepared in the manner described in the preferred embodiments and examples. A preferred method for preparing the LC-TII of the present invention is by hydration of mixtures of DO-NGPE and CPT and mild hand-shaking.

Certain compositions may be particularly distinct and advantageous when the target cell, its localization, or the amount of drug delivered is important. Alternatively the topoisomerase I inhibitor may be mixed with other agents including other lipids to form a heterogenous micellar-liposome suspension, a micelle in liposome suspension, or a pure liposome suspension. These agents might include stabilizers, e.g. buffers, surfactants other lipids or combinations of lipids, other therapeutic agents, and the like.

The present invention also includes a method of treating cells wherein the lipid formulations of TII are used to introduce a pharmacologically effective amount of a topoisomerase-I inhibitor to a target cell in a pharmaceutically acceptable carrier. For use with the present invention the term "pharmacologically effective amount" is within the range of 1 to 20 mg/kg in humans.

The liposome drug or micellar-drug complex may be introduced into contact with cells by a variety of methods. As used herein the terms "contact", "contacted", and "contacting", are used to describe the process by which an effective amount of a topoisomerase I inhibitor, e.g., CPT, comes in direct juxtaposition with the target cell. In cell culture, the micelles can simply be dispersed in the cell culture solution. The topoisomerase I inhibitor-lipid complex can be introduced into a cancer cell by preparing a topoisomerase-inhibitor/lipid complex; and contacting or treating cancer cells with a pharmacologically effective amount of the topoisomerase-inhibitor/lipid complex.

Certain embodiments of the use of the claimed LC-TII involve the killing of cells in vitro. The mitosis-arresting ability of the claimed compounds renders them useful for permanently or transiently arresting cells in the G2 of mitosis. Using the claimed micellar topoisomerase-inhibitor complex, one of ordinary skill in the art will be able to enrich a population of non-cycling cells relative to a population of cycling cells. Further, one of ordinary skill in the art will be able to purify tissue samples of actively cycling cells. For in vitro applications, the complex is typically introduced into the cell-containing media.

A particularly preferred target for the method of treatment are those located within a multicellular organism, with a mammalian organism being particularly preferred. A most preferred organism is a patient suspected of having cancer, with a human patient being most preferred.

For in vivo applications, the LC-TII are typically injected intravenously. In order to allow drug delivery into cells that are not accessible through intravenous injection, it is possible to directly inject the LC-TII, e.g., LC-CPT, complexes into a specific location in an animal's body. For example, injection via a catheter into the arterial wall may be used. In a preferred use the present invention is resuspended in a pharmaceutically acceptable carrier and delivered by injection intraperitoneally. Alternatively, the LC-TII containing a camptothecin family member are injected directly into a site comprising cells in need of therapy.

Those of skill in the art will recognize that the best treatment regimens for using camptothecin to suppress neoplastic or cancerous growth can be straightforwardly determined. This is not a question of experimentation, but rather one of optimization, which is routinely conducted in the medical arts. In vivo studies in nude mice provide a starting point from which to begin to optimize the dosage and delivery regimen. The frequency of injection may initially be approximately once a week, conducted as demonstrated in the studies disclosed herein. However, this frequency might be optimally adjusted from one day to every two weeks to monthly, depending upon the results obtained from the initial clinical trials and the needs of a particular patient.

The present invention also comprises kits for the introduction of camptothecin into a target cell comprising the lipid/drug complex of the present invention. The kit may contain a composition comprising a micellar camptothecin complex composed of a lipid and a topoisomerase-I inhibitor. In a particularly preferred embodiment the lipid comprises either alone or in combination a lipid with unsaturated fatty acids and a cationic lipid.

The preferred use for the LC-TII is to treat a multiple cellular organism, with mammalian organisms being more preferred, and humans being most preferred. The most preferred camptothecin genus member is the closed ring, or lactose form, of camptothecin. However, other TIIs such as topotecan, 9-aminocamptothecin, 9-nitrocamptothecin, 9-chloro-10, 11-methylenedioxy (20S)-camptothecin (CMC), CPT-11, and SN 38 are also preferred.

Following long-standing patent construction practice, the word "a" and "an" denote "one or more" when used in regards to this disclosure, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Drug Complexation efficiency of DO-NGPE micelles as a function of lipid:drug ratio FIG. 2A. Cellular viability of DIFI cells treated with LC-CPT at the 24 hour timepoint. A: Lipid; B: CPT; C: L-CPT; and D: L+CPT.

DETAILED DESCRIPTION OF THE PREFERRED EMBODIMENTS

Figure 2A:
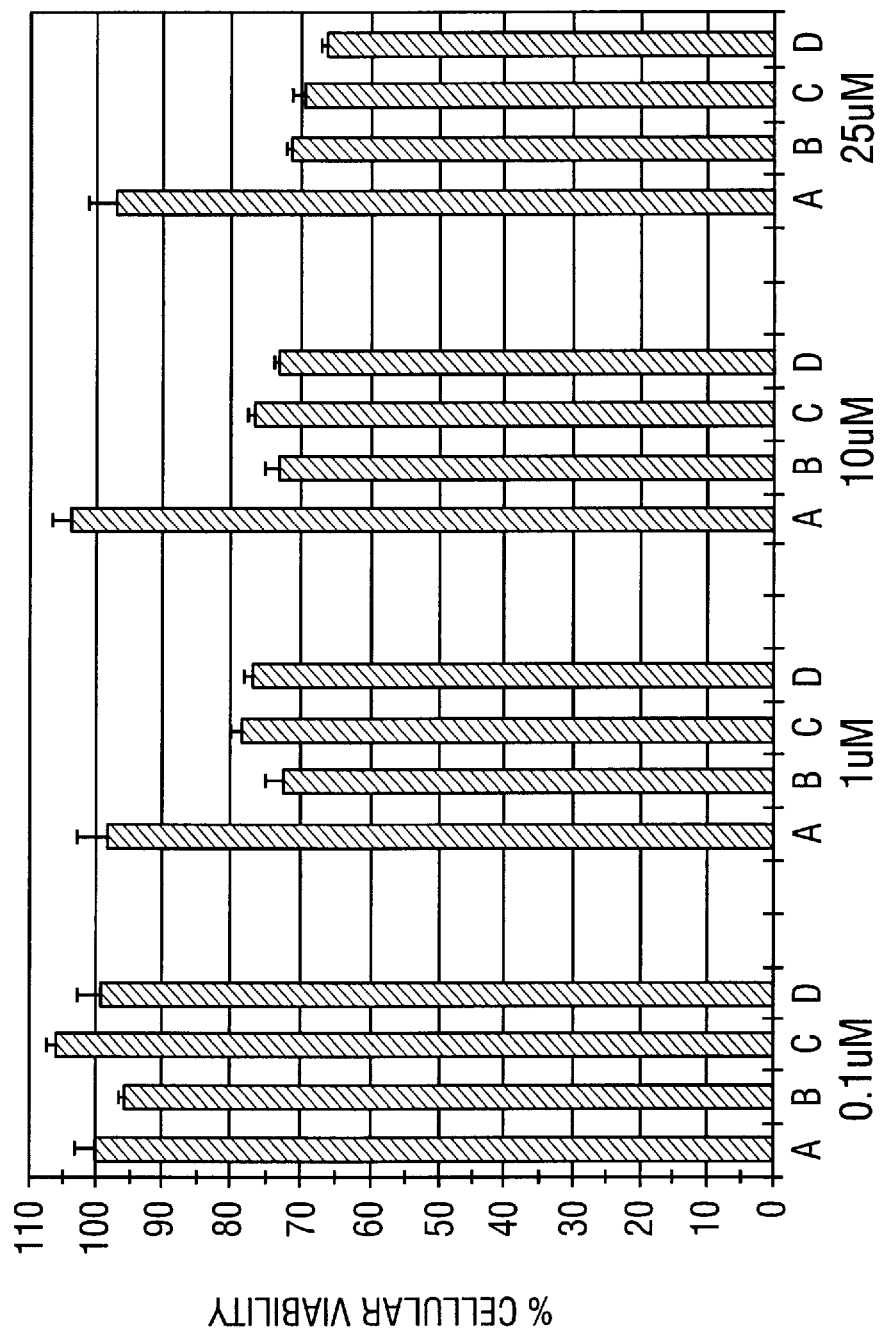
FIG. 2B. Cellular viability of DIFI cells treated with LC-CPT at the 48 hour timepoint. A: Lipid; B: CPT; C: L-CPT; and D: L +CPT.
FIG. 2C. Cellular viability of DIFI cells treated with LC-CPT at the 120 hour timepoint. A: Lipid; B: CPT; C: L-CPT; and D: L +CPT.

The present invention is a formulation of lipid-bound camptothecin (CPT) that is simple to produce, achieves a high binding efficiency, and has demonstrated activity equivalent to that of the free compound against several human tumor cell lines. In the intraperitoneal treatment of P388 and L1210 leukemia, LC-CPT has demonstrated increased potency compared to the free compound.

The development of a lipid/drug complex that provides for an efficient entrapment of camptothecin family topoisomerase I inhibitors and maintains its cytotoxicity comparable to that of the free fully-active compound is very important. The lipid complexed-camptothecin (LC-CPT) formulation demonstrates activity equivalent to that of the free compound against several human tumor cell lines and has approximately twice the in vivo potency of free CPT in the intraperitoneal treatment of P388 leukemia in mice. The lipid complexed topoisomerase I inhibitor composition has improved biodistribution, pharmacokinetics and both in vitro and in vivo activity against activity cycling tumor and other actively cycling cells.

Although CPT is the prototype of topoisomerase I inhibitors, it has been difficult to work with due to its poor aqueous solubility. Some lipophilic drugs such as taxol and taxotere can be solubilized by mild detergents, surfactants and alcohol- containing solutions; however, no similar vehicle has been identified for CPT lactone. Even when prepared in solutions containing DMSO, Tween-20, cremophor, and methanol, crystallization and precipitation of drug occurs. Solutions containing chloroform and methanol can solubilize CPT, but are too toxic for clinically relevant studies.

By using anionic lipids that have been found to be nontoxic in concentrations necessary for complex formation, TIIS will form a smooth suspension amenable for in vitro and in vivo study. While the inventors have not identified the exact nature of the TII:lipid particles, their size and chromatographic features suggest the formation of micellar structures or submicroscopic lipid-drug aggregates. However, knowledge of the exact physical characterization of the structure of the lipid-drug complex is not important to the invention. Kotting et al. have shown that depending on the nature of the lipid used, micelles will accumulate in lung, kidney, liver, and to some extent brain. Kwon et al. have shown that polymer-drug conjugates containing polyethylene glycol form micelles that demonstrated prolonged circulation in blood and enhanced uptake at target sites.

The formulation of a lipid-complexed preparation allows for the intravenous delivery of this compound. LC-TII, in the formulation described, appears to have equivalent antitumor activity to free CPT in the treatment of KB-VI, MDA-Panc3, and DIFI cell lines. The antitumor effect appears to rely upon prolonged drug exposure, but is not affected by MDR-1 expression. LC-CPT has increased potency in vivo and a more predictable pattern of biodistribution than free CPT. This is probably related to crystallization of the free drug since CPT (lactone ring intact) is a highly lipophilic molecule. The increase in potency of LC-TII compared to free CPT was predicted by Burke et al. who demonstrated that lipid membranes stabilize the lactone ring. However, the present invention allows for lipid: drug ratios for lower than the lipid: drug ratios employed by Burke et al. thereby rendering clinical usage of the claimed LC- TII possible. Furthermore, interactions with lipids may reduce albumin binding which has been shown to reduce CPT activity.

Studies of the biodistribution of this formulation of L-CPT intravenously administered to mice demonstrates the greatest concentration of drug in lung tissue. This is followed by accumulation in liver and spleen. Since these organs are the most common sites of metastatic tumor deposits, LC-CPT may provide the additional benefit of organ targeted therapy. Similarly, distribution of drug away from the bladder and gastrointestinal tract may reduce toxicity at these sites.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Abbreviations

Some of the abbreviations used in this patent are as follows:
LC-Lipid Complexed
TII-Topoisomerase I Inhibitor
CPT-Camptothecin
NGPE-N-Glutaryl-Phosphatidylethanolamine (18:1)
DOPG-1,2-Dioleoyl-sn-Glycero-3-[Phospho-rac-(1-glycerol)]
DOTAP-1,2-Dioleoyl-3-Trimethylammonium-Propane
DMPC-1,2-Dimyristoyl-sn-Glycero-3-Phosphocholine
DOPC-1,2-Dioleoyl-sn-Glycero-3-Phosphocholine
DOPE-1,2-Dioleoyl-sn-Glycero-3-Phosphoethanolamine
PC—sn-Glycero-3-Phosphocholine
TOPPA-1,1',2,2'-Tetraoleoyl Pyro Phosphatidic Acid
OCPC-1-Oleoyl-2-Capryl-sn-Glycero-3-Phosphocholine
DMPG-1,2-Dimyristoyl-sn-Glycero-3-[Phospho-rac-(1-glycerol)]

EXAMPLE I

Liposome Complexation

In order to prepare LC-CPT (a liposomal preparation containing CPT within spherical lipid vesicles) various individual lipids were screened for complexation with CPT. Individual lipids that complex well with CPT can be combined to form liposomal CPT. CPT crystals and lipid/CPT complexes of >0.4 microns can be visualized under a fluorescent microscope (since CPT fluoresces due to its rigid ring structure). CPT that does not complex with lipid is seen as fluorescent crystals, while CPT that complexes with lipid is seen as morphologically different fluorescent particles (lipid/CPT complexes). Therefore, the better a lipid complexes with CPT the less CPT crystals are formed, and the more lipid/CPT complexes are formed.

Materials and Methods

Chemicals and Drugs. CPT is obtainable from Dr. Vishnuvajjala (National Cancer Institute). Cardiolipin (CL), DO-N-Glutaryl-phosphatidylethanolamine (NGPE), and all other lipids were obtained from Avanti Polar Lipids, Inc (Alabaster, AL). [$^3$H] CPT is obtainable from Moravek Biochemicals, Inc. (Brea, Calif.) [$^{14}$C] Cholesterol from Amersham Corp.

Cell Lines. MDA-Panc3 cells(pancreas carcinoma), DiFi cells (colon carcinoma), and KB cells (squamous carcinoma) were used for in vitro data.

Drug/lipid Complex Preparation. CPT was mixed in ratios of from 2:1 to 25:1 w/w lipid:drug in chloroform-methanol (8:1). For studies where CPT was radiolabeled, approximately 0.02 uCi/ml [$^3$H] CPT was added to the preparation. Trace quantities of $^{14}$C labeled cholesterol was added to samples requiring lipid labeling. For small samples, the lipids were dried in 12×75 mm culture tubes under a stream of nitrogen gas. For large samples, a rotavapor (Buchi RE140, Switzerland) was used to dry lipids in a 100 to 1000 ml round bottom flasks. The lipophilic film was then vortexed in a Touch Mixer Model 231 (Fisher Scientific, Fair Lawn, N.J., U.S.A.) for one minute in sterile phosphate buffered saline (pH 7.4). For liposomal CPT 0.9% Nace was used. Preparations were screened for lipid entrapment by light and fluorescent microscopy (Nikon Labophot-2, Japan).

Chromatography. A 30 cm agarose 0.5M column is used to separate liposome-bound drug from free CPT. PBS is used as the mobile phase for all preparations. Twenty samples were collected in 3 mL aliquots for a total of 60 mLs. Fluorescence and scintigraphy were used to detect encapsulated and free drug. Fluorimetry. Aliquots of 20 μl from each collection tube were transferred to cuvets containing 2 ml methanol. Fluorimetry was performed as described by Hart et al. (Hart et al., 1969). Fluorescence was measured at an excitation wavelength of 370 nm and emission wavelength of 434 nm (Perkin-Elmer MPF44A, Norwalk, Conn., U.S.A.). Two ml of ethanol was used as a control for machine calibration.

Determination of Entrapment Efficiency.

A modification of the Ficoll flotation method for separating entrapped from free drug was used (Fraley et al.). 200 L samples were added to 12×75 mm culture tubes. One ml of 30% Ficoll was layered on the liposome preparation, then one ml of PBS was layered on top of the Ficoll. The tube was spun for 30 min at 3400 rpm in Sorvall GS2-B swing rotor. The percent entrapment was calculated with the formula:

$$\% \text{ entrapment}: \frac{\text{(amount drug associated with lipid)}}{\text{(total starting amount of drug)}} \times 100$$

Table 1 demonstrates the interaction between CPT and lipids of varying carbon chain length, charge, and saturation (as screened by fluorescent microscopy for lipid entrapment) alone and in various combinations. Of those tested the most favorable interaction was seen with DO-NGPE, which led to higher CPT solubility after interaction to form micellar/drug complexes.

TABLE 1

Lipids investigated for complexation with CPT

| Lipid | Chain length /Saturation | | Charge | Crystals | % bound to CPT |
|---|---|---|---|---|---|
| Dicaproyl PC | 6:0, | 6:0 | 0 | yes | <5 |
| Dimyristoyl PC | 14:0, | 14:0 | 0 | yes | <5 |
| Distearoyl PC | 18:0, | 18:0 | 0 | yes | <5 |
| 1-Stearoyl, 2-Myristdyl PC | 18:0, | 14:0 | 0 | yes | <5 |
| 1-Stearoyl, 2-Oleoyl PC | 18:0, | 18:1 | 0 | yes | <5 |
| Dimyristoyl PG | 14:0, | 14:0 | −1 | yes | <5 |
| Dioleoyl PG | 18:1, | 18:1 | −1 | no | <5 |
| Cardiolipin | * | | −2 | no | |
| Dioleoyl-NGPE | 18:1, | 18:1 | −2 | no | |

*natural product 18:2 (90.3%), 18:1 (6.5%), 16:0 (1%), 16:1 (1%), 16:0 (1%)
Note: Each lipid with the prefix Di- (or the number deisgnation 1-, 2-) contains two fatty acyl chains connected to a head group (examples of head groups are PC, PG, NGPE). Chain length refers to the number of carbons in the fatty acyl chain (capropyl contains 6 carbons, myristoyl contains 14 carbons, stearoyl contains 18 carbons, oleoyl contains 18 carbons etc . . . ). The saturation of the fatty acyl chain refers to how many double bonds the fatty acyl chain contains. For example, the fatty acyl chain capropyl is saturated (it contains no double bonds, therefore its saturation number is 0. Dicarproyl PC (chain length: saturation written as 6:0, 6:0) contains two fatty acyl chains (both carpoyl chains). The chain length is 6 carbons and the saturation is 0 there are no double bonds).

Lipids of varying carbon chain length, charge, and saturation, alone or in different combinations, were empirically screened for their ability to form liposomes incorporating CPT by fluorescent microscopy. Table 1 shows the different lipids used. All combinations of neutral lipids or with DPMG resulted in massive presence of drug crystals mixed with numerous but barely fluorescent liposomes, indicating a marked lack of affinity or compatibility of CPT for lipid bilayers as previously reported.

In contrast, the use of DOPG alone resulted in an important observation: lack of drug crystallization and presence of only a few fluorescent particles by fluorescence microscopy, thus suggesting drug solubilization or formation of small lipid-drug particles or micelles. Chromatographic evaluation confirmed that <5% of CPT was incorporated in the liposome fraction of the preparation, the rest presumably being solubilized or in small particles not detectable by fluorescence microscopy.

These observation led the present inventors to other negatively charged lipids. Cardiolipin and DO-NGPE (FIG. 2) used alone contain double negative charges, and were found to result in homogeneous and milky preparations devoid of drug crystals and containing only a few fluorescent particles compatible with multilamellar liposomes that could be eliminated by sonication. Chromatographic evaluation of these preparations confirmed again that <5% of CPT eluted with the liposome fraction, the rest of the drug eluting later in a large number of consecutive fractions. By differential centrifugation, the lipid-binding efficiency of cardiolipin was about 67% and that of DO-NGPE 97%. DO-NGPE-CPT was, therefore, selected for further biological and pharmacological studies.

Physically, there is a bimodal distribution particle size distribution in the DO-NGPE-CPT complex. The majority of particles (98%) had a mean diameter of 23.8 nm (range, 20.8–28.5 nm), the remaining fraction had a mean diameter of 153 nm. (range, 123.3–208.1 nm). Therefore, the vast majority of particles were undetectable by light or fluorescent microscopy. Although larger particles were visualized by fluorescent microscopy, column chromatography demonstrated that only a small fraction of drug was present in these vesicles. The small particle diameter was consistent with the lack of crystallization of LC-CPT (DO-NGPE/CPT complex) observed.

EXAMPLE II

In Vitro Cytotoxicity

Material and Methods

Cytotoxicity Assay. 8,000 cells/well in 135 ul of Dubelco's MEM with 10% fetal bovine serum (FBS) was added to 96-well culture plates. The plates were incubated for 14 h at 37° in the presence of 5% $CO_2$. 15 L of CPT, liposomal CPT (L-CPT), and empty liposomes (ELs) with CPT were added in concentrations of 1.0–500 M CPT. Lipids were added to each sample (5–25:1 lipid:drug weight ratio). The cells were incubated in the presence of drug for 24 to 120 h. After 15 L of 5 mg/ml MTT in PBS was added to the samples, the cells were incubated at 37° for 2 h. 100 L of lysis buffer (50 ml DMF, 20 gm SDS, to total volume 100 ml with water, adjusted to pH 4.7 with NaOH) was added to each well. Plates were incubated for 14h at 37°, then read at 570 nm in a kinetic microplate reader. A dose of 0.1 M blank lipid was used as a control for 100% survival.

Results

LC-CPT consisting of 12.5:1 DO-NGPE:CPT was used for in vitro assays of cytotoxicity. Lethal cellular injury induced by CPT requires prolonged exposure, cytotoxicity of L-CPT and controls were determined at 24, 72, and 120 hr intervals of continuous drug exposure.

Figure 2B:
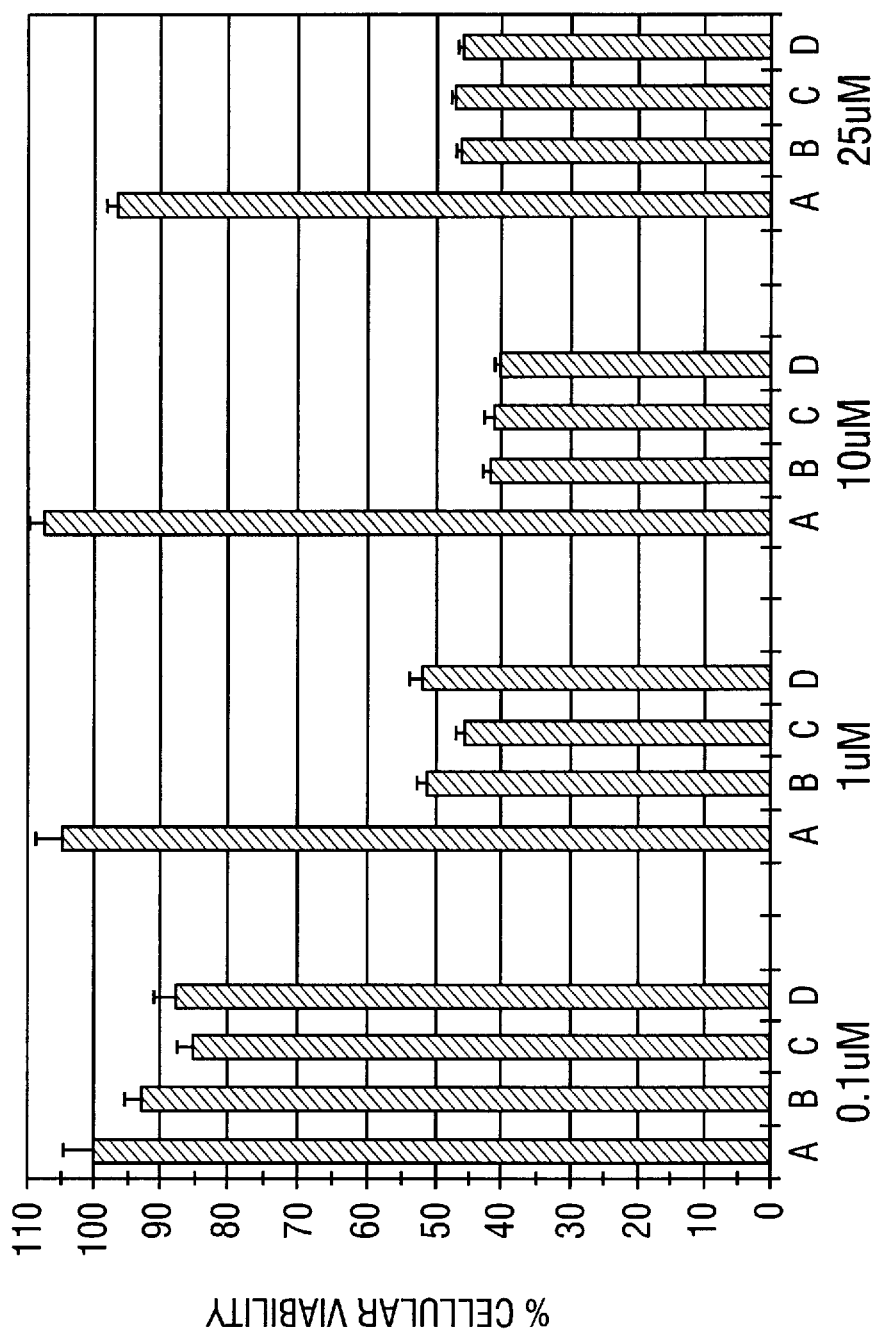
Figure 2C:
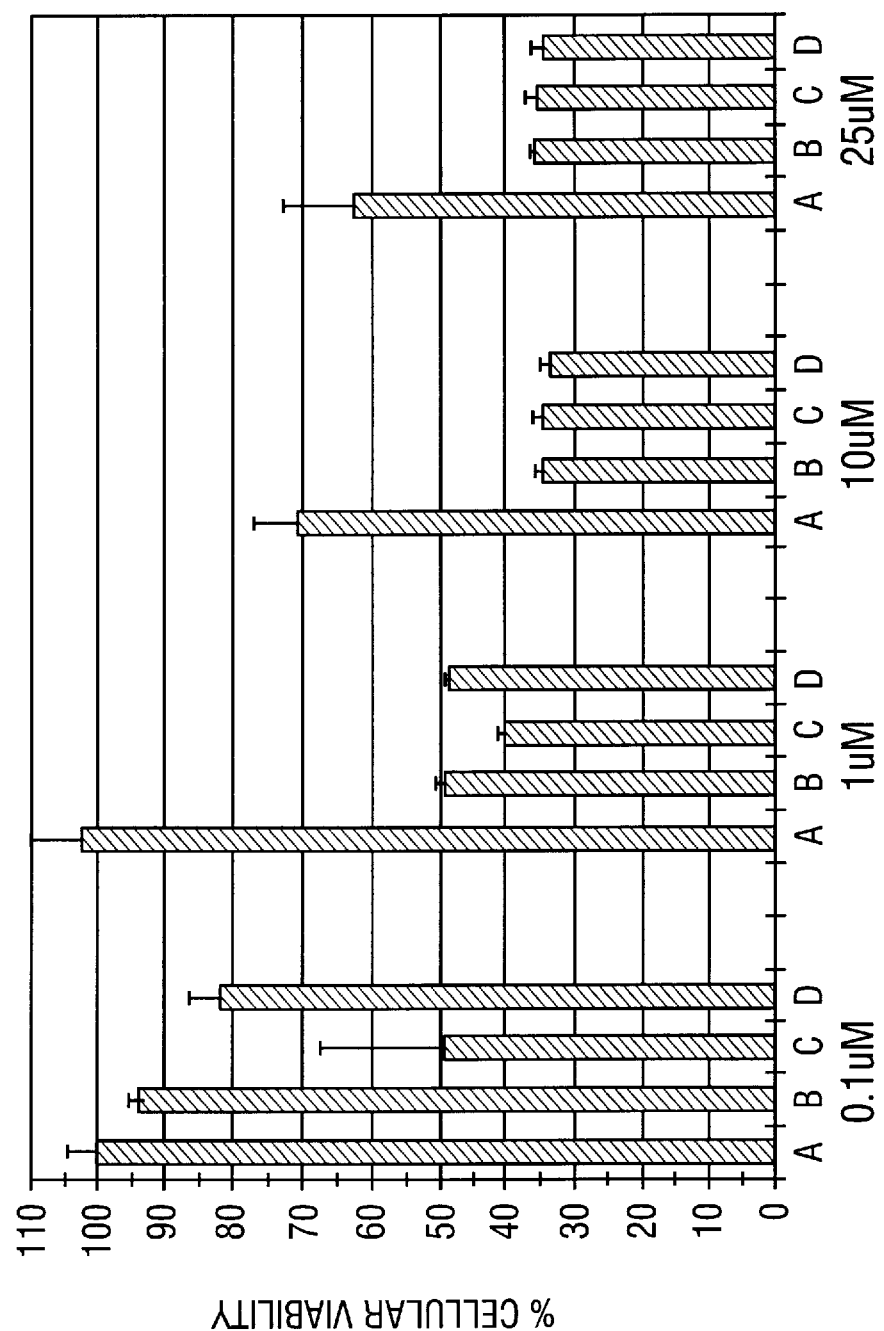
Figure 3A:
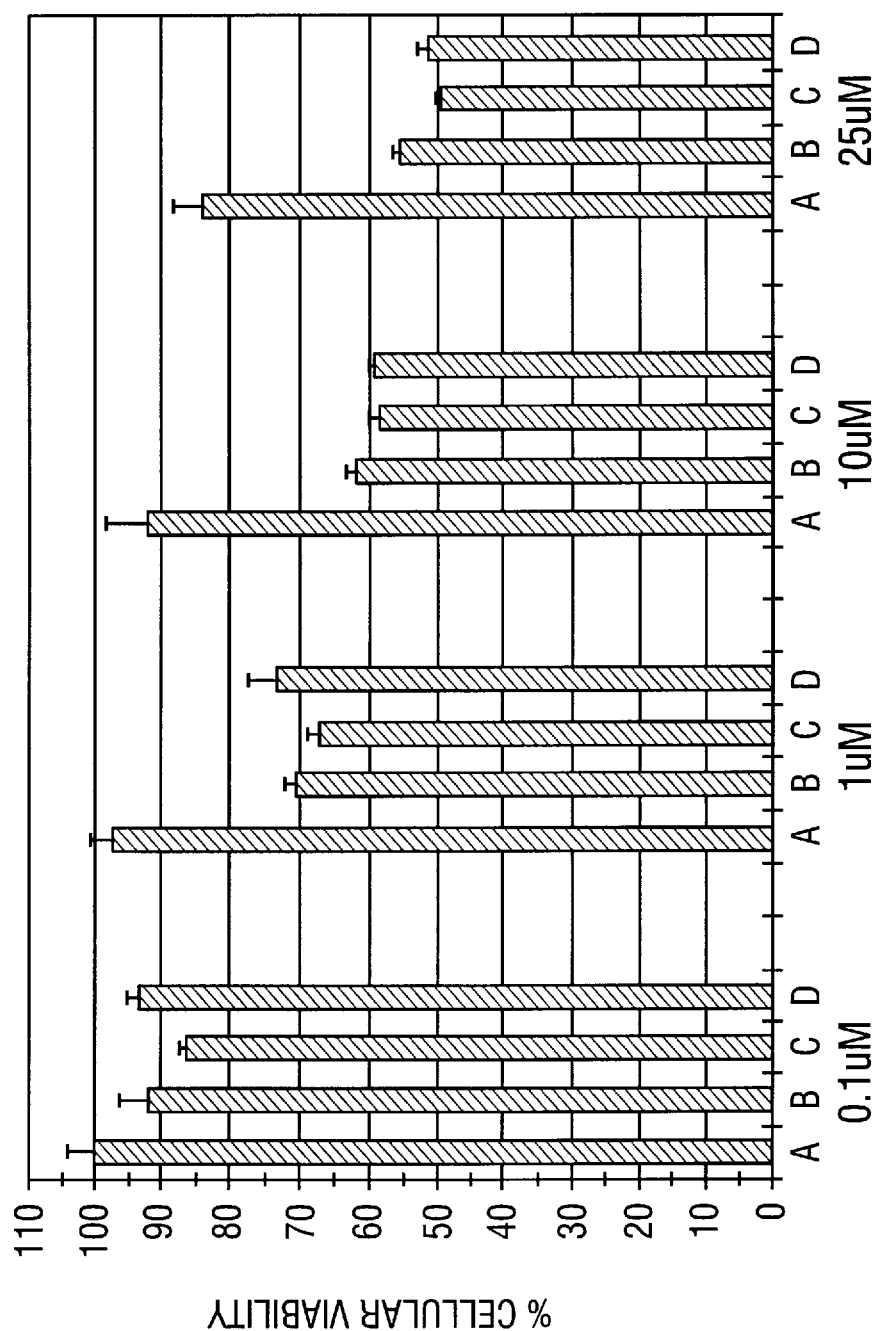
FIG. 3A. Cellular viability of KB cells treated with LC-CPT and Controls at the 24 hour timepoint. A: Lipid; B: CPT; C: L-CPT; and D: L +CPT.
Figure 3B:
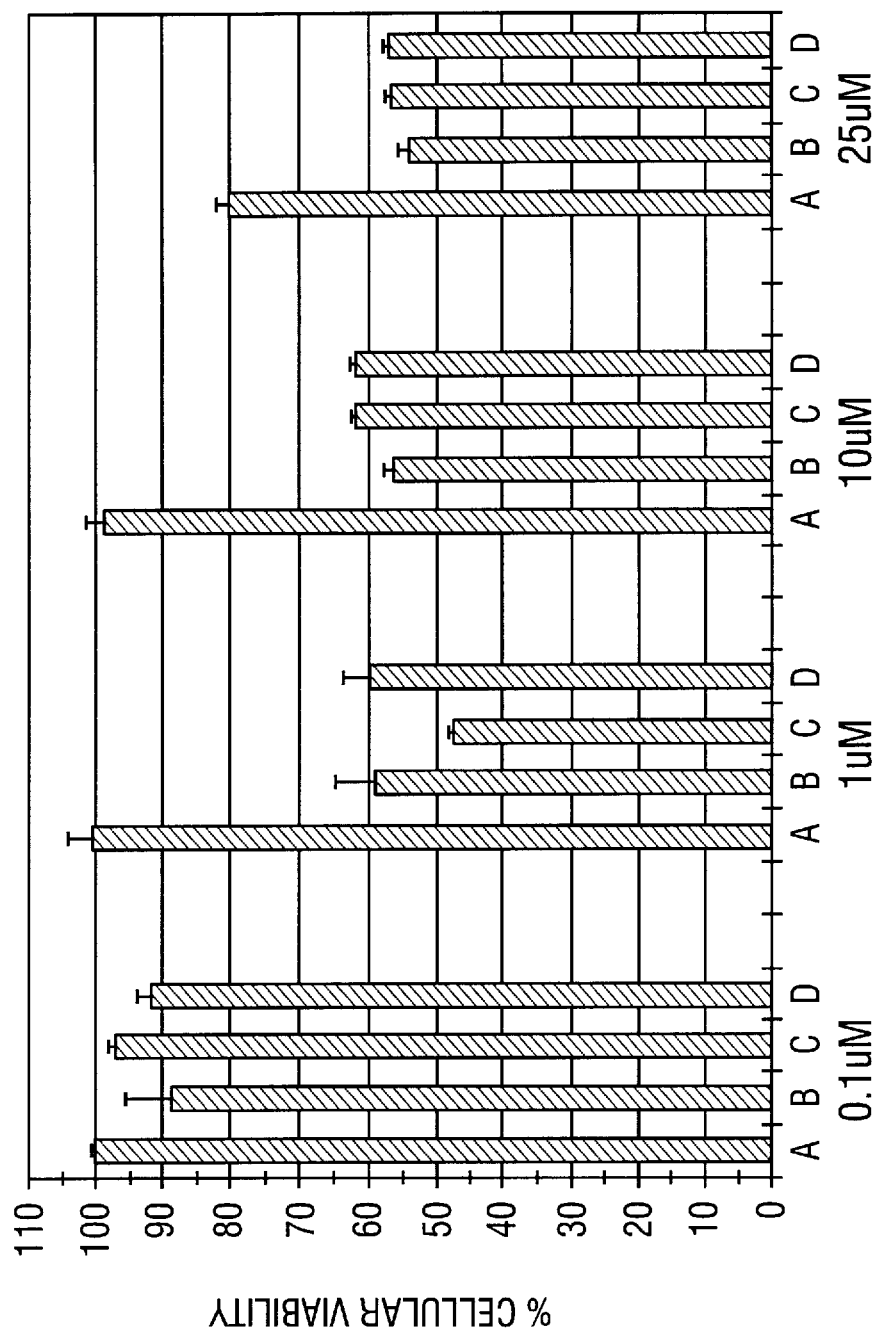
FIG. 3B. Cellular viability of KB cells treated with LC-CPT and Controls at the 48 hour timepoint. A: Lipid; B: CPT; C: L-CPT; and D: L+CPT.
Figure 3C:
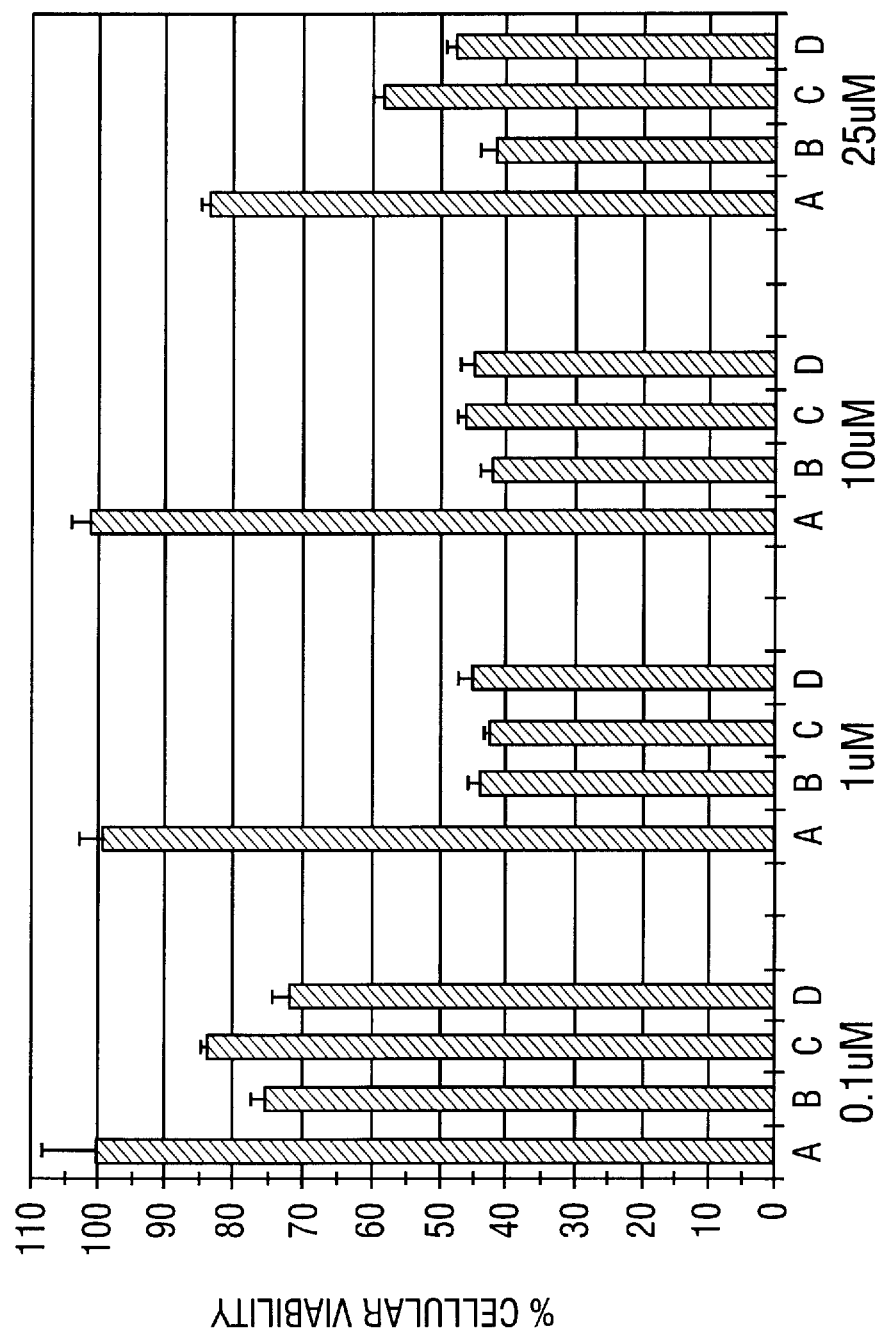
FIG. 3C. Cellular viability of KB cells treated with LC-CPT and Controls at the 120 hour timepoint. A: Lipid; B: CPT; C: L-CPT; and D: L +CPT.

FIGS. 2A through 2C demonstrate the effect of CPT, L-CPT, Lipid blanks (no CPT), and lipid blanks plus unentrapped CPT (L+CPT) on the cytotoxicity of DIFI cells at 24, 72, and 120 h incubation time points. Of note, blank liposomes exhibit little cytotoxicity. CPT is significantly more toxic to cells at a concentration of 1M compared to 0.1M, but further increases in CPT did not lead to a significant increase in cytotoxicity. L-CPT demonstrates toxicity similar to that of the free drug. While there was a marked decrease in cellular viability between 24 and 72 h of drug exposure, there was less of a change in viability between the 72 and 120 h time points. In FIGS. 3A through 3C, KB cellular viability is plotted as a function of drug exposure from 24–120 h. It appears that KB cells are somewhat more sensitive to CPT at 24 h than DIFI cells, however at 120 h a similar cellular viability of approximately 40% is noted. MDA-Panc3 cells are modestly sensitive to free and entrapped CPT at 24 h. There is a marked reduction in viability between 24 and 72 h, but no significant increase in cytotoxicity is appreciated between 72 and 120 h. Again, the entrapped and free drugs appear to be equipotent. DO-NGPE does not appear to have any intrinsic antitumor activity and does not inhibit the effects of CPT.

Figure 4A:
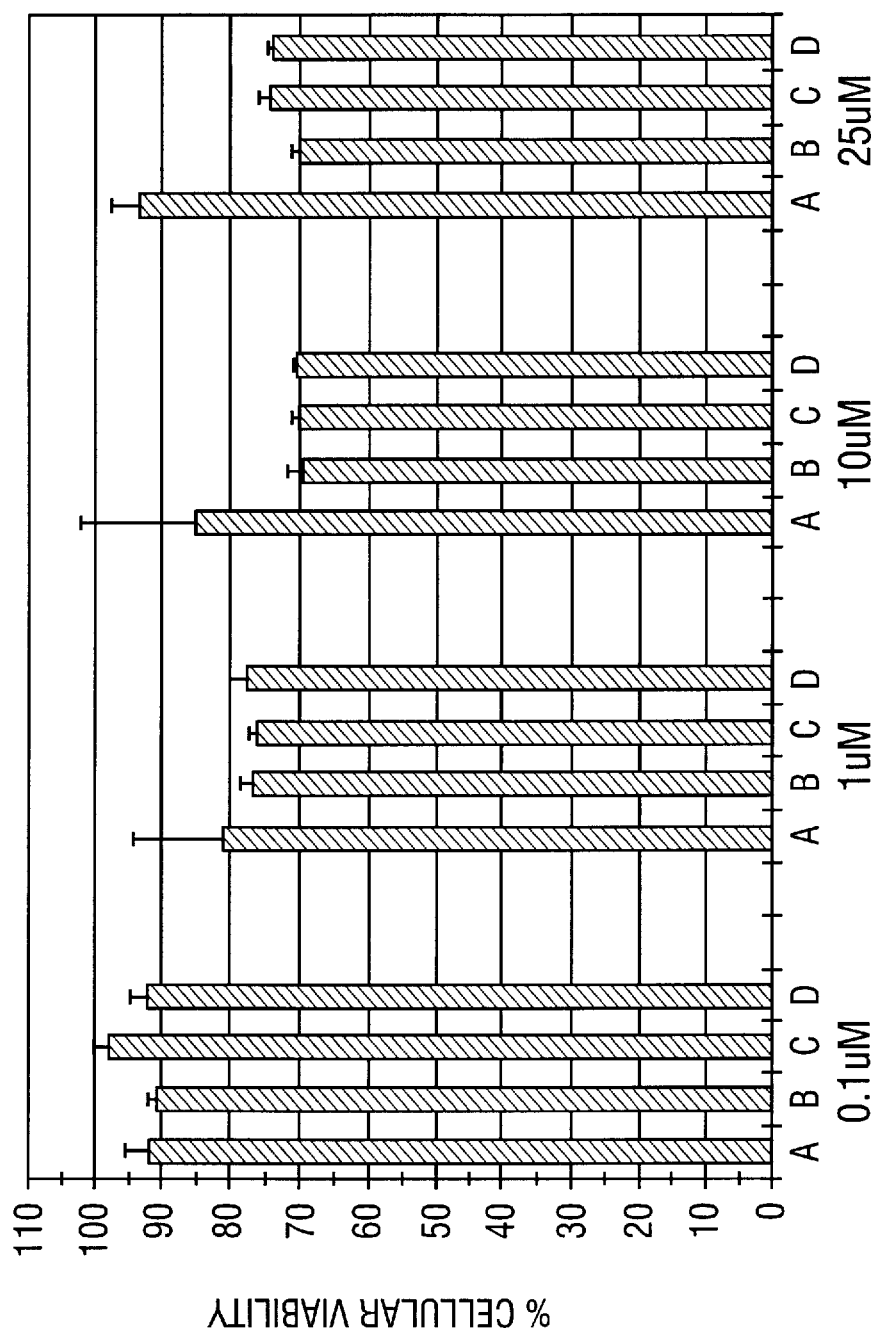
FIG. 4A. Cellular viability of PANC3 cells treated with LC-CPT at the 24 hour timepoint. A: Lipid; B: CPT; C: L-CPT; and D: L+CPT.
Figure 4B:
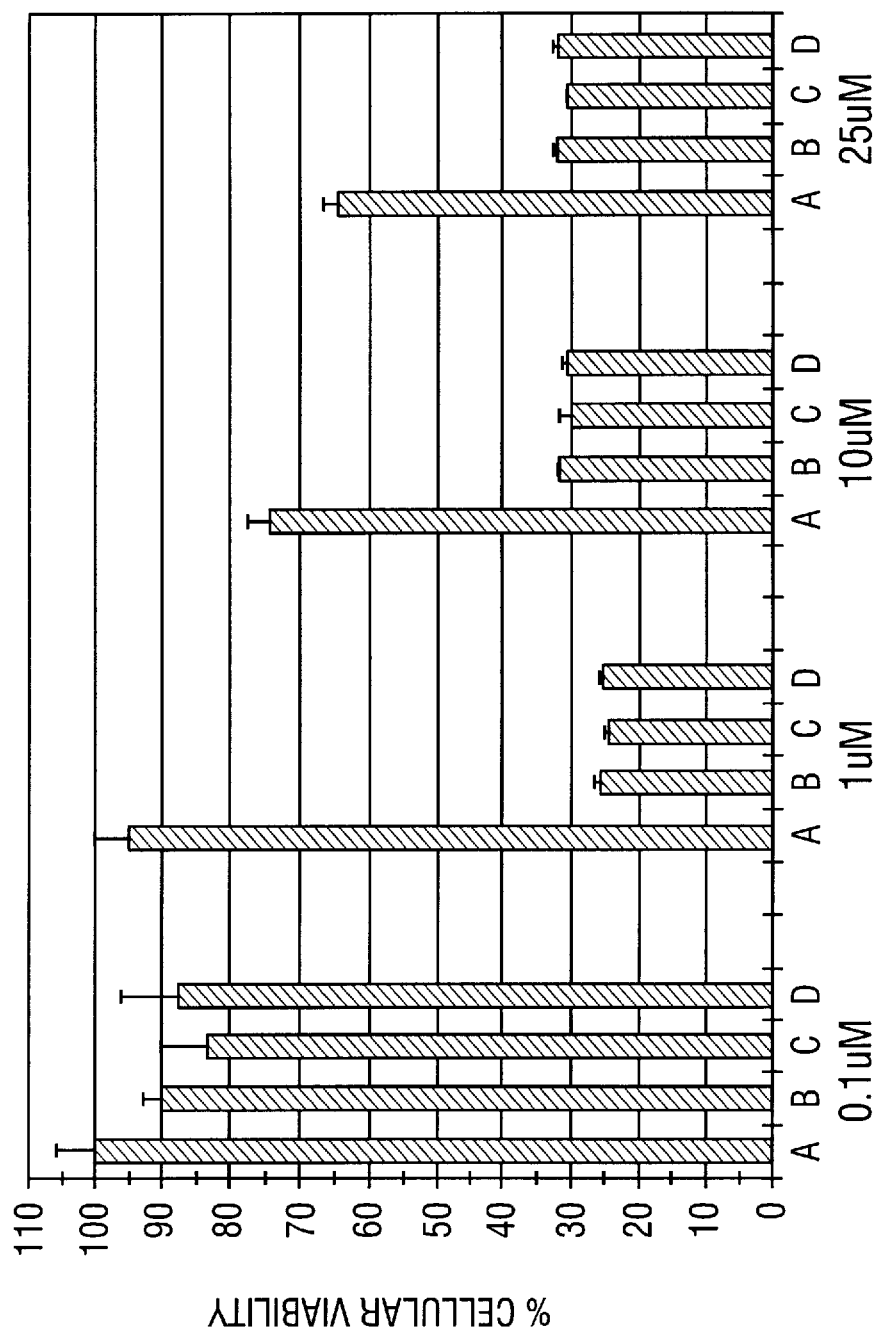
FIG. 4B. Cellular viability of PANC3 cells treated with LC-CPT at the 48 hour timepoint. A: Lipid; B: CPT; C: L-CPT; and D: L+CPT.
Figure 4C:
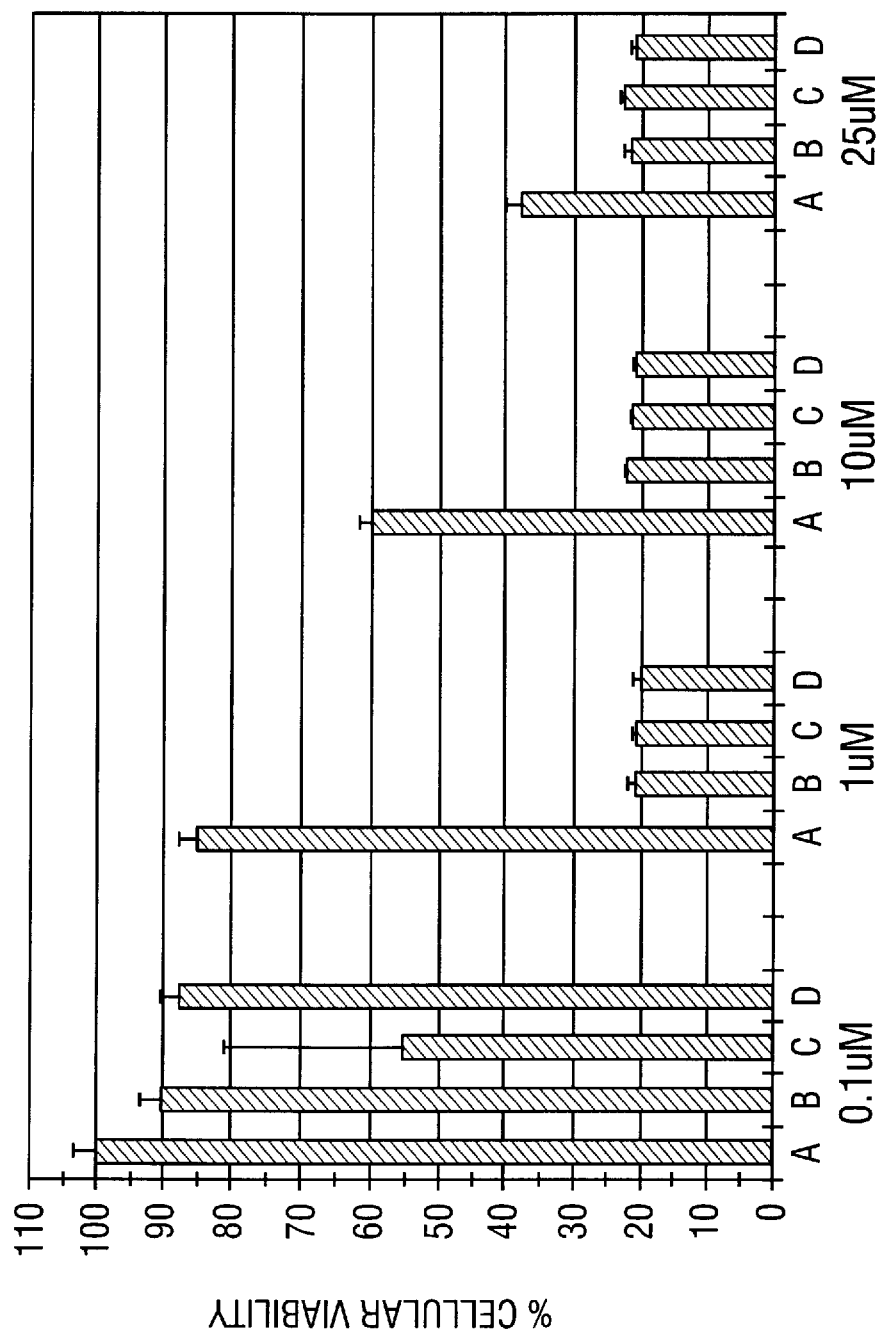
FIG. 4C. Cellular viability of PANC3 cells treated with LC-CPT at the 120 hour timepoint. A: Lipid; B: CPT; C: L-CPT; and D: L+CPT.

Lethal cellular injury induced by CPT was enhanced by prolonged exposure. FIG. 4A through 4C demonstrate the effect of CPT, LC-CPT, lipid blanks (no CPT), and lipid blanks plus unentrapped CPT (LC+CPT) on the cytotoxicity of MDA-Panc3 cells at 24 and 120 h incubation time points. Of note, blank liposomes exhibit little cytotoxicity. CPT is significantly more toxic to cells at a concentration of 1 $\mu$mol compared to 0.1 $\mu$mol, but further increases in concentration did not lead to a significant increase in cytotoxicity. LC-CPT demonstrates toxicity similar to that of the free drug. Increasing the duration of exposure from 24 to 120 h significantly increases the cytotoxic effect. It appears that MDA-Panc3 cells are somewhat more sensitive to CPT at 24 h than DIFI cells.

To determine if MDR-1 phenotype would have an effect on cellular sensitivity to LC-CPT, KB-3-1 cells sensitive and KB-VI cells, multidrug resistant, were exposed to concentrations of 1 to 25 $\mu$ mol LC-CPT. It was found that similar cytotoxicity was seen for most concentrations of CPT; however, when exposed to 25 $\mu$mol LC-CPT, KB-VI cells were slightly more resistant than KB-3-1 cells. L-CPT, in the formulation described, appears to have equivalent efficacy to CPT in the treatment of KB, MDA-Panc3, and DIFI cell lines. The antitumor effect appears to be optimal when cells are exposed to drug for 72 h with little additional effect seen over the ensuing 48 h.

EXAMPLE III

Liposomal Camptothecin

To increase the cytotoxic effects of LC-CPT relative to CPT, lipid must surround (encapsulate) the CPT to protect it from inactivation. Since the cytotoxicity of LC-CPT was similar to that of the free drug, the CPT was not encapsulated by the lipid (DO-NGPE). Encapsulation (and concomitant protection from inactivation) can be accomplished by surrounding CPT in a liposome (a unilamellar or multilamellar structure). As demonstrated by Table 2, the DO-NGPE:CPT ratio can be adjusted. Decreasing the lipid-drug ratio to 2:1 eliminates excess DO-NGPE (excess DO-NGPE that does not form complexes with CPT), producing purely the drug/lipid complexes (LC-CPT) described previously. Therefore, LC-CPT appears to only contain enough lipid to form micellar aggregates of CPT or to form a hydrophobic scaffold for CPT-CPT aggregation.

The inventors attempted to protect the CPT from inactivation by surrounding the existing DO-NGPE:CPT complex with a liposome (Table 3) or by adding another lipid to DO-NGPE to form a liposome. Since each DO-NGPE molecule has two negative charges on its head group, a positively charged (cationic) lipid was tried. A cationic lipid can be used either to surround LC-CPT or to intercalate with the DO-NGPE to form a liposome. The saturated fatty acid Stearylamine did combine with DO-NGPE to form a clearly fluorescent liposome with few CPT crystals present (Table 3). The liposomes formed were very unstable under the heat of the microscope, they broke leaving fluorescent, crystalline CPT. Since Stearyamine did not form stable liposomes, but showed some promise, other cationic lipids were examined. The lipid DOTAP contains a positively charged head and also contains two oleoyl (18 : 1) fatty acyl chains-group already shown by Table 1 to be important in complexation with CPT. Therefore, it was investigated.

DOTAP complexes well with CPT (Table 2) and forms fluorescent liposomes with CPT, yet when DOTAP is combined with DO-NGPE no liposomes are formed. Therefore, if DOTAP was used with CPT, DO-NGPE is not a desirable component of the liposomes. This led to the exploration of other Dioleoyl (18 : 1) compounds that would complex with CPT (see DOPC, DOPE, DOPG, Dielaidoyl PC) in Table 2. As Table 2 shows, DOTAP, DOPE, and Dielaidoyl PC complex well with CPT. This discovery led to the exploration of Dioleoyl compounds that when combined could both complex with CPT and form liposomes (liposomal CPT). This led to the following formulations (Table 3): (DOPG : DO-NGPE : CPT, DOPE : DOPC : CPT, and DOPC : DOPG : CPT). All of these above formulations form liposomes, but still contain a few CPT crystals. Table 4 follows the same reasoning using mole % ratios of dioleoyl lipids to form liposomal CPT. A liposomal CPT preparation, DOPE : DOPC : DOTAP (40%, 40%, 20%) contains fluorescent liposomes of CPT and very few, if any, CPT crystals. The DOPE:DOPC:DOTAP formulation is a milky liposomal suspension that contains liposomes of various size 5 (75% of the preparation is smaller than one micron in diameter). The larger liposomes fluoresce slightly, while the smaller liposomes (that cannot be seen) aggregate into larger fluorescent liposomes over time.

TABLE 2

Lipid Complexation with CPT Mg Ratios (Lipid:CPT)

| Lipid | Chain Length: Saturation | Complexes with CPT by Fluorescent Microscopy | CPT Crystals |
|---|---|---|---|
| DO-NGPE:CPT | | | |
| 12.5:1 (DO-NGPE:CPT) | 18:1, 18:1 | ++ | few |
| 10:1 (DO-NGPE:CPT) | 18:1, 18:1 | ++ | few |
| 4:1 (DO-NGPE:CPT) | 18:1, 18:1 | ++ | few |
| 2:1 (DO-NGPE:CPT) | 18:1, 18:1 | +++ | few |
| Other lipids with two 18:1 (chain length:saturation) fatty acyl chains: | | | |
| 12.5:1 (DOPG:CPT) | 18:1, 18:1 | + | few |
| 12.5:1 (DOPC:CPT) | 18:1, 18:1 | ++ | few |
| 12.5:1 (DOPE:CPT) | 18:1, 18:1 | +++ | few |
| 12.5:1 (DOTAP:CPT) | 18:1, 18:1 | +++ | few |
| 12.5:1 (Dielaidoyl PC :CPT) | 18:1, 18:1 (9-trans, 9-trans) | +++ | none |
| 12.5:1 (TOPPA:CPT) | 18,1:18:1, 18:1, 18:1 | − | many |
| Miscellaneous lipids with (different length:saturation) fatty acyl chains: | | | |
| 12.5:1 (DMPC:CPT) | 14:0, 14:0 | − | many |
| 12.5:1 (Petroselinoyl PC:CPT) | 18:1, 18:1 (6-cis, 6-cis) | ++ | few |
| 12.5:1 (OCPC:CPT) | 18:1, 6:0 | + | many |
| 12.5:1 (Dipalmitoleoyl PC:CPT) | 16:0, 18:1 | + | many |

*Note: Dioleoyl lipids contain one double bond (unsaturated) at the 9 carbon. This double bond is in the cis configuration. Dielaidoyl PC contains one double bond at the 9 carbon, but in the trans configuration. Similarly, Petroselinlyl PC contains one double bond, but at the 6 carbon the double bond is in the cis configuration).

TABLE 3

Liposomal CPT Formulations (Molar Ratios)

| Lipids | Molar Ratios | Liposomes Formed | Complexes with CPT | CPT Crystals |
|---|---|---|---|---|
| DO-NGPE:Stearylamine Formulations: | | | | |
| DO-NGPE: Stearylamine: | CPT 1:1:1 | yes | +++ | few |

TABLE 3-continued

Liposomal CPT Formulations (Molar Ratios)

| Lipids | Molar Ratios | Liposomes Formed | Complexes with CPT | CPT Crystals |
|---|---|---|---|---|
| DO-NGPE: Stearylamine: CPT | 1:1.5:1.5 | yes | +++ | few |
| DO-NGPE: Stearylamine: CPT | 2:3:3 | no | ++ | few |
| DO-NGPE: Stearylamine: DMPC:CPT | 1:1:1:1 | yes | − | many |
| DO-NGPE: Stearylamine: Cholesterol:CPT | 1:1.5:1.5:1.5 | yes | − | many |
| DO-NGPE:DOTAP Formulations: | | | | |
| DO-NGPE:DOTAP:CPT | 1.5:1.5:1 | no | ++ | few |
| DO-NGPE:DOTAP:CPT | 3:3:1 | no | ++ | few |
| DO-NGPE Miscellaneous Lipid Formulations: | | | | |
| DO-NGPE:DMPC:CPT | 1:4:1 | yes | + | many |
| DO-NGPE:DMPC:CPT | 1:1:1 | yes | ++ | few |
| Dioleoyl Formulations: | | | | |
| DOPE:DOPC:CPT | 1:1:1 | yes | ++ | few |
| DOPE:DOPC:CPT | 7:3:1 | yes | ++ | many |

TABLE 4

Liposomal CPT Formulations (Mol. % lipids + 1 Mg CPT)

| Formulation | Mol. % | Liposomes Formed | Complexes with CPT | CPT Crystals |
|---|---|---|---|---|
| DOTAP | 20% | yes | ++ | few |
| DMPC | 25% | | | |
| NGPE | 55% | | | |
| DOTAP | 20% | no | +++ | few |
| DOPG | 25% | | | |
| egg PC | 55% | | | |
| DMPC | 55% | no | ++ | few |
| DOPG | 25% | | | |
| DOTAP | 20% | | | |
| DOPC | 55% | yes | + | many |
| DOPG | 25% | | | |
| DOTAP | 20% | | | |
| DOPE | 40% | yes | ++++ | none |
| DOPC | 40% | | | |
| DOTAP | 20% | | | |
| OCPC | 40% | yes | + | few |
| DOPC | 40% | | | |
| DOTAP | 20% | | | |
| OCPC | 40% | yes | + | few |
| DOPG | 40% | | | |
| DOTAP | 20% | | | |
| DOPE | 40% | yes | ++ | few |
| Dielaidoyl PC | 40% | | | |
| DOTAP | 20% | | | |

Based on the above, a preferred formulation for CPT is DOPE, DOPC, DOTAP (mol. % 40, 40, 20). This formulation complexes well with CPT, and small vesicles are formed (as is evident from freeze-fracturing). The vesicles have been sized in the range of 50 nm. to 1 μm (1 micron) in diameter. This formulation also does not sediment, but remains for weeks as a turbid suspension. Of course modifications of this formulation, and equivalents of it are anticipated to work equally well, if not better.

EXAMPLE IV

In vitro Utilities

Those of ordinary skill in the art will understand that the lipid complexed topoisomerase I inhibitors of the present invention will have various in vitro utilities. TII inhibitors are used in a variety of applications known to the art, and the LC-TII of invention may be employed in any of these applications. In fact, the LC-TII will enjoy advantages over non-complexed TII, because more of the TII will remain in the more active closed ring form.

Topoisomerase I inhibitors result in the arresting of cells in the G2 phase of mitosis. A high concentration of the LC-TII will permanently arrest cells at G2 until the time of cell death. Lower concentrations of LC-TII may be used to transiently arrest cells at G2.

Because of the mitosis-arresting ability of the LC-TII, these compounds can be used to rid cell populations of cells which are actively cycling by arresting the active cells in the G2 phase and eventually killing them. Those of skill in the art will understand that some populations of tumor cells are actively cycling cells. Therefore, in a mixed population of cells, it is possible to treat with the claimed LC-TII to remove the actively cycling cells. As such, the LC-TII are useful in order to enrich a population of non-cycling cells relative to a population of cycling cells.

The LC-TII can be used to purify tissue samples. For example, a sample from a tumor can be treated with the LC-TII to rid it of the actively cycling tumor cells. In this manner, one can obtain a population of cells enriched in non-actively cycling, for example fibroblasts. This is but one example of how the LC-TII of the present invention can be used to selectively delete and/or enhance populations of cells relative to other populations of cells.

Based on the above, those of ordinary skill in the art will understand that the LC-TII of the invention provide valuable tools for the scientific researcher.

The utility of the LC-TII for killing cells in culture is conclusively demonstrated by the data in Example II and FIGS. 2–4. The methods employed in Example II detail various ways in which to treat cells with LC-TII.

EXAMPLE V

In Vivo Antitumor Activity of LC-TII

Figure 5A:
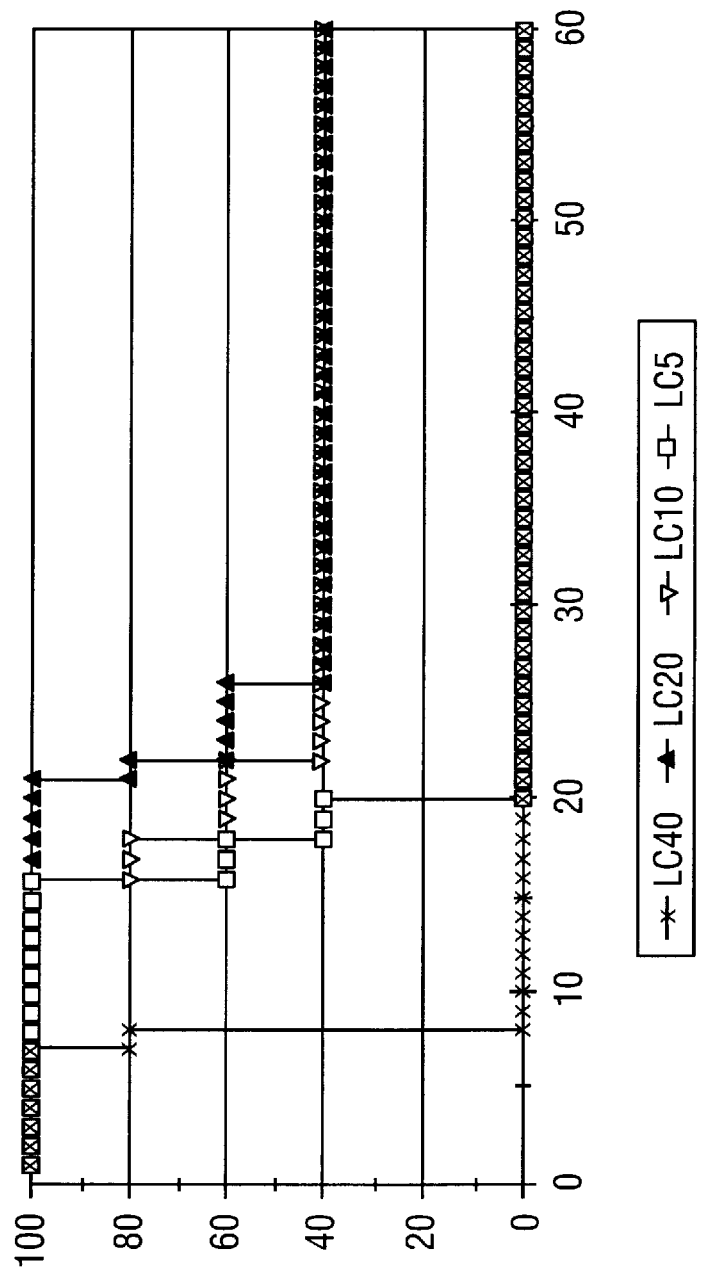
FIG. 5A. Survival of mice inoculated with the P388 cell line treated with LC-CPT.
Figure 5B:
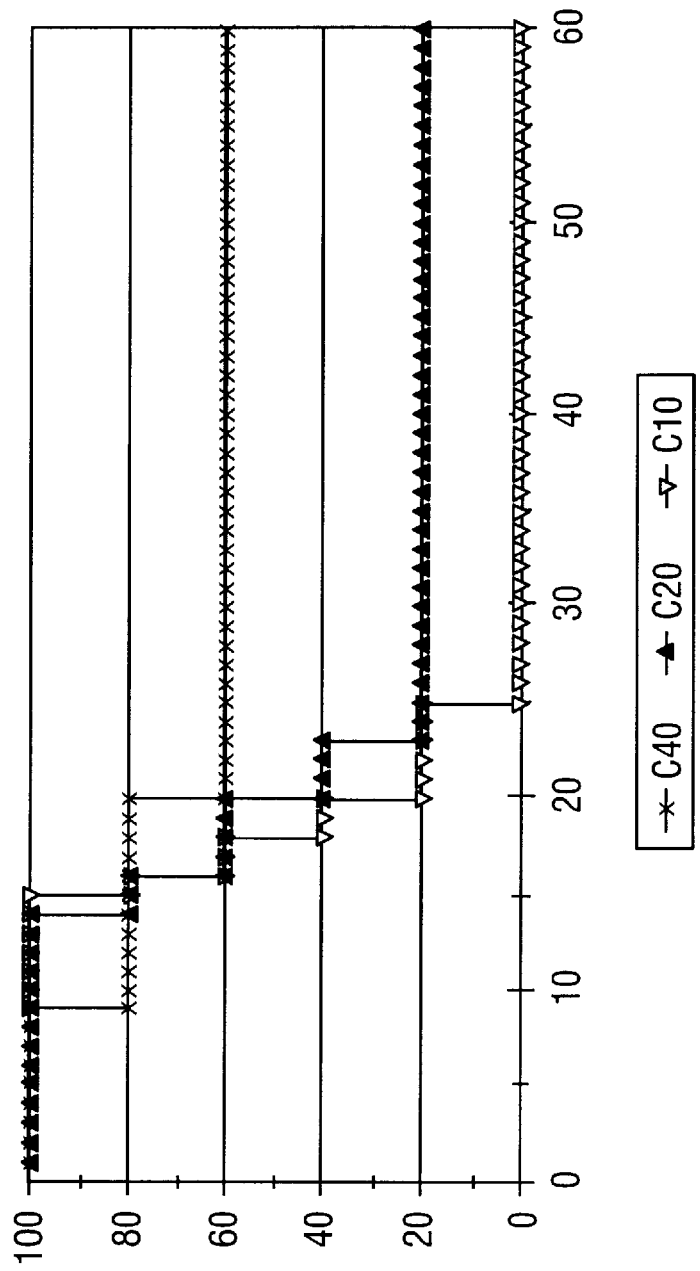
FIG. 5B. Survival of mice inoculated with the P388 cell line treated with CPT.

The in vivo effects of LC-TII were demonstrated on mice carrying a tumor burden that were treated with varying amounts of camptothecin and control liposomes and survival data for mice which were: 1) untreated, 2) received blank lipids (without drug), or 3) received 20 mg/Kg free CPT plus the corresponding amount of blank lipids (12.5:1 w/w) were obtained (FIG. 5a). Of the 13 mice that did not receive CPT, twelve expired between days 13 and 20, indicating tumor related death. The single survivor received an inadequate inoculation of tumor cells. Of the mice treated with free CPT, there were three (60%) long-term survivors at a dose of 40 mg/Kg and one at 20 mg/Kg (20%). There was one treatment related death (day 8) at the 40 mg/kg dose level (FIG. 5b).

Materials and Methods

In Vivo Protocol. B6D2F1 mice (Charles River Laboratories, Wilmington, Mass., U.S.A.) were injected with 106 L1210 leukemia cells via the intraperitoneal route. A single intraperitoneal treatment with ELs, CPT, L-CPT, ELs +CPT was administered 24 hours after tumor inoculation. Five animals were used in each group except for the control group which consisted of 7 untreated mice.

Statistical Considerations. Animal survival data was plotted using the method described by Kaplan and Meier (Kaplan and Meier, 1958):

$$(1 - CPM^P/cPM_S) \times 100\%$$

where $CPM^S$=cpm of starting material and $CPM^P$=cpm of pellet.

Results

Figure 5C:
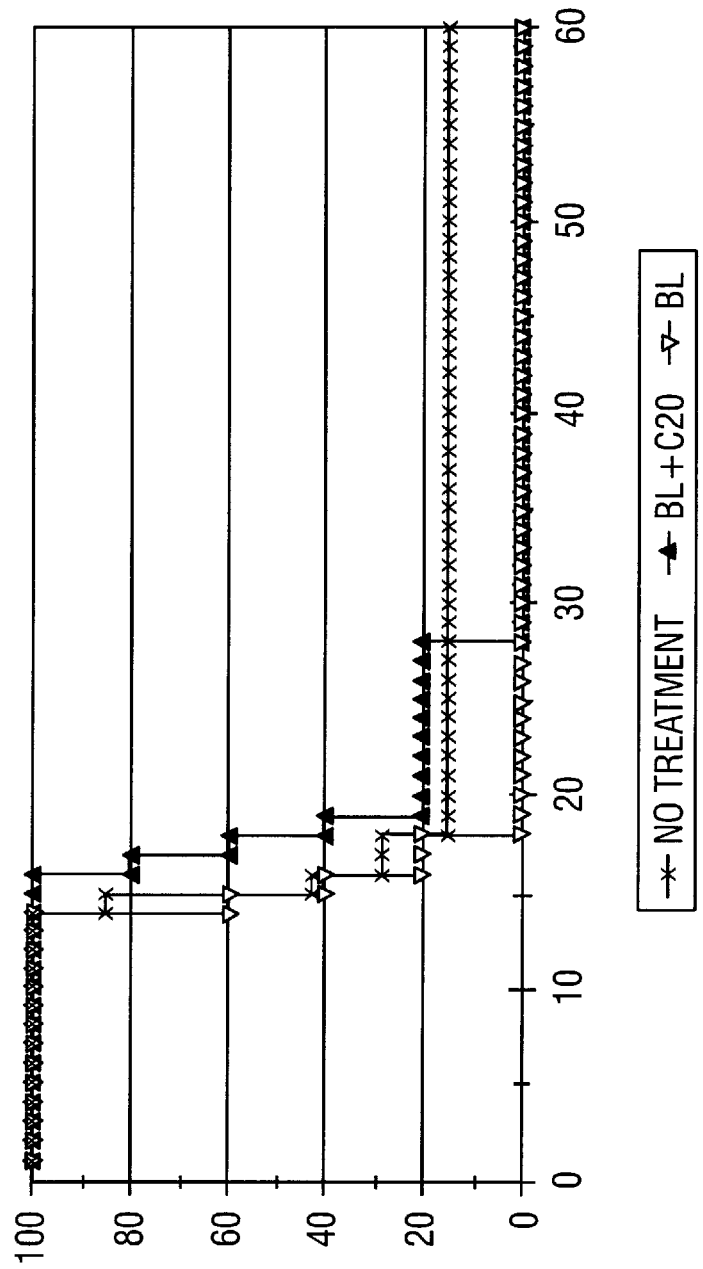
FIG. 5C. Survival of mice inoculated with the P388 cell line treated with control.

To demonstrate the survival data for mice inoculated with P388 leukemia mice were treated with LC-CPT, free CPT or lipid plus free CPT (unentrapped). Table 5 and FIGS. 5A through 5C demonstrate that LC-CPT and free CPT displayed similar antitumor activity (%T/C 186 vs. 207); however, LC-CPT was about 2-fold more potent. of the mice treated with free CPT, the optimal dose was 40 mg/kg with a %T/C of 2.7 and 3 animals were long-term survivors. No activity was observed with a dose of 20 mg/kg (%T/C=100). Of the mice treated with LC-CPT, there was a significantly shortened survival for the mice treated with a dose of 40 mg/kg due to toxicity, which suggests that lipid binding increases the potency of CPT. The optimal doses were 20 mg/kg and 10 mg/kg with %T/Cs of 186 and 150 respectively. There were no treatment-related deaths in the mice treated with either dose of LC-CPT and there were two (40%) 50-day survivors in each group, but none in the corresponding groups receiving free CPT suggesting increased potency for the lipid complex formation.

TABLE 5

Mice treated IP with LC-CPT, L + CPT (lipid + unentrapped CPT) or lipid alone 24 h after IP injection with $10^6$ P388 cells.

| Treatment | Dose CPT (mg/kg) | % T/C | 50-day survivors |
|---|---|---|---|
| LC-CPT | 40 | 50 | |
| LC-CPT | 20 | 186 | 2/5 |
| LC-CPT | 10 | 150 | 2/5 |
| LC-CPT | 5 | 121 | |
| CPT | 40 | 207 | 3/5 |
| CPT | 20 | 100 | |
| CPT | 10 | 121 | |
| L + CPT | 20 | 121 | |
| Lipid* | 20 | 100 | |

*Lipid dose equivalent to 20 mg/kg LC-CPT

Against L1210 leukemia, LC-CPT displayed significant activity (%T/C=146 at 20 mg/kg) while free CPT was inactive. Because LC-CPT appeared to have improved potency compared to free CPT and LC-CPT caused early death at the highest doses, mice inoculated with L1210 leukemia were treated with doses of 30 to 60 mg/kg free CPT or 10 to 20 mg/kg of LC-CPT (Table 6). All animals treated with LC-CPT survived longer than those treated with free CPT and two of the animals treated with LC-CPT were 50-day survivors. One animal treated with 15 mg/kg free CPT plus lipid survived 50 days.

TABLE 6

Mice treated IP with LC-CPT, CPT, L + CPT (lipid + unentrapped CPT) or lipid alone 24 h after IP injection with $10^6$ L1210 cells.

| Treatment | Dose CPT (mg/kg) | % T/C | 50-day survivors |
|---|---|---|---|
| LC-CPT | 20 | 146 | 1/5 |
| LC-CPT | 15 | 100 | 1/5 |
| LC-CPT | 10 | 123 | 0 |
| CPT | 60 | 92 | 0 |
| CPT | 45 | 85 | 0 |
| CPT | 30 | 85 | 0 |
| L + CPT | 20 | 85 | 0 |
| L + CPT | 15 | 100 | 1/5 |
| L + CPT | 10 | 85 | 0 |
| Lipid* | 20 | 92 | 0 |

*Lipid dose equivalent to 20 mg/kg LC-CPT

All mice treated at the highest dose level of L-CPT (40 mg/kg CPT) died of toxicity within the first eight days of treatment. There did not appear to be any toxic deaths at doses of 20 mg/kg or less. Forty percent of the mice treated with 20 mg/Kg and 10 mg/Kg L-CPT were cured. All mice treated with 5 mg/Kg L-CPT died between 17 and 20 days indicating suboptimal treatment of their intraperitoneal leukemia.

Since CPT (lactone ring intact) is a highly lipophilic molecule, the lipid complexation preparation allows for the intravenous administration of this compound. Since it has been shown that membrane entrapment prevents opening of the lactone ring, and that the closed-lactone form of CPT has 10 fold the activity of its sodium salt, the observation that L-CPT has enhanced potency when compared to the free compound was not completely unsuspected.

EXAMPLE VI

Biodistribution

The interaction of CPT with lipids has a profound effect on the biodistribution of CPT is shown in Table 7. Both free CPT and LC-CPT were rapidly cleared from the blood. CPT and LC-CPT achieved highest concentrations in the lungs and gastrointestinal tract, respectively. Drug tissue levels were consistently lower in mice treated with LC-CPT, even in the GI tract. Drug levels with free CPT were about 180-fold higher than LC-CPT in the lungs which is apparently due to embolization of crystallized free drug into the lungs followed by a depot effect.

TABLE 7

Organ distribution of free CPT and LC-CPT after i.v. administration of 10 mg/kg CPT

| Organ | Time (hrs) | Free CPT ($\mu$g/ml or $\mu$g/mg dry tissue) | LC-CPT ($\mu$g/ml or $\mu$g/mg dry tissue) |
|---|---|---|---|
| Blood | 6 | 0.069 ± 0.039 | 0.010 ± 0.001 |
| GI Tract | 6 | 2.562 ± 0.515 | 2.208 ± 0.090 |
| Heart | 6 | 1.458 ± 0.555 | 0.047 ± 0.001 |
| Kidney | 6 | 0.443 ± 0.164 | 0.072 + 0.005 |
| Liver | 6 | 2.077 ± 0.402 | 0.672 ± 0.051 |
| Lung | 6 | 38.217 ± 3.061 | 0.209 ± 0.009 |
| Blood | 24 | 0.008 ± 0.012 | ND* |
| GI Tract | 24 | 0.492 ± 0.148 | .059 ± .054 |
| Heart | 24 | 0.228 ± 0.092 | .006 ± .002 |
| Kidney | 24 | 0.539 ± 0.428 | .004 ± .001 |
| Liver | 24 | 0.429 ± 0.124 | .006 ± .001 |
| Lung | 24 | 12.276 ± 5.363 | .004 ± .002 |

*ND, Not detectable

Heart and kidney levels of free CPT were higher than those of LC-CPT. Interestingly, gastrointestinal concentrations of drug were consistently greater than hepatic concentrations; presumably due to the rapid processing of LC-CPT in the liver and elimination via the gut. The significant variability associated with injection of free drug was attributed to its poor aqueous solubility.

EXAMPLE VII

Pharmaceutical Compositions

The present invention can be formulated into a aqueous compositions (inocula) comprising an effective amount of the LC-TII dissolved or dispersed in a pharmaceutically acceptable aqueous medium. Such compositions are also referred to as inocula. Pharmaceutically acceptable compositions and excipients are described herein for use with the LC-TII and refer to molecular entities and compositions that do not produce an allergic or similar untoward reaction when administered to a human.

The preparation of an aqueous composition that contains an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A preparation can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Typically, the inventors prepare the LC-TII of the present invention by hydration of a mixture of the lipid and drug with gentle hand shaking.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580).

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLE VIII

Human Therapy Treatment Protocols

This example is concerned with human treatment protocols using the LC-TII combination disclosed above. It is proposed that LC-TII treatment will be of use in the clinical treatment of various human diseases and disorders in which transformed or cancerous cells play a role. It is considered to be particularly useful tool in anti-tumor therapy, for example, in treating patients with solid tumors and hematological malignancies.

Methods of treating such patients using lipid:drug complexes have already been formulated, for example, see incorporated herein by reference. It is contemplated that such methods may be straightforwardly adapted for use with the LC-TII described herein. As discussed above, other therapeutic agents could be administered either simultaneously or at distinct times. One may therefore employ either a pre-mixed pharmacological composition or "cocktail" of the therapeutic agents, or alternatively, employ distinct aliquots of the agents from separate containers.

The various elements of conducting a clinical trial, including patient treatment and monitoring, will be known to those of skill in the art in light of the present disclosure. The following information is being presented as a general guideline for use in establishing LC-TII clinical trials.

It is contemplated that patients chosen for the study would have failed to respond to at least one course of conventional therapy and had to have objectively measurable disease as determined by physical examination, laboratory techniques, or radiographic procedures. Such patients should also have no history of cardiac or renal disease and any chemotherapy should be stopped at least 2 weeks before entry into the study.

In regard to LC-TII administration, it is considered that certain advantages will be found in the use of an indwelling central venous catheter with a triple lumen port. The LC-TII complexes should be filtered, for example, using a 0.22 $\mu$m filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87 to 99%, and adjustments for agent loss can then be accounted for.

The LC-TII may be administered over a short infusion time or at a steady rate of infusion over a 7 to 21 day period. The infusion given at any dose level should be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of LC-TII should be administered to groups of patients until approximately 60% of patients showed unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory tests should include complete blood counts, serum creatinine, creatine kinase, electrolytes, urea, nitrogen, SGOT, bilirubin, albumin, and total serum protein.

To evaluate the anti-tumor responses, it is contemplated that the patients should be examined at 4–8 week intervals. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all valuable tumor nodules or at least 1 month with no tumor sites showing enlargement. Similarly, a mixed response may be defined by a reduction of the product of perpendicular diameters of all measurable lesions by 50% or greater with progression in one or more sites.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Burke TG, Staubus AE, Mishra AK. Liposomal stabilization of Camptothecin's lactone ring. J Am Chem Society 114:8318–8319, 1992.

Fraley R, Subramani S, Berg P, and Papahadjopoulos D. J Biol Chem 255: 10431.

Giovanella BC, Hinz HR, Kozielski AJ, et al. Complete growth inhibition of human cancer xenografts in nude mice by treatment with 20-(S)-Camptothecin. Cancer Res 51: 3052–3055, 1991.

Gottlieb JA, Guarino AM, Call JB, et al. Preliminary pharmacologic and clinical evaluation of camptothecin sodium (NSC-100880). Cancer Chemother Rep 54: 461–470, 1970.

Hart LG, Call JB, and Oliverio VT. A fluorometric method for determination of camptothecin in plasma and urine. Cancer Chemother Rep 53: 211–214, 1969.

Hertzberg RP, Caranfa MJ, Holden KG, et al. Modification of the hydroxy lactone ring of camptothecin: Inhibition of mammalian topoisomerase I and biological activity. J Med Chem 32: 715–720, 1989.

Hsiang YH, Hertzberg R, Hecht S, et al. Camptothecin induces protein-linked DNA breaks via mammalian DNA topoisomerase I. J Biol Chem 260: 14873–14878, 1985.

Hsiang YH and Liu LP. Identification of mammalian topoisomerase I as an intracellular target of the anticancer drug camptothecin. Cancer Res 48: 1722–1726, 1988.

Kaplan EL and Meier P. Non-Parametric estimation from incomplete observations. J Am Stat Assoc 53: 457–481, 1958.

Kohn KW, Jackman J, O° Connor PM. Cell cycle control and cancer chemotherapy. J Cell Biochem 54:440–452, 1994.

Mattern MR, Mong SM, Bartus HF, et al. Relationship between the intracellular effects of camptothecin and the inhibition of DNA topoisomerase I in cultured L1210 cells. Cancer Res 47: 1793–1798, 1985.

Moertel CG, Schutt RJ, Reitemeier RJ, and Hahn RG. Phase II study of camptothecin (NSC-100880) in the treatment of advanced gastrointestinal Cancer.Cancer Chemother Rep 56: 95–101, 1972.

Muggia FM, Creaven PJ, Hansen HH, et al. Phase I clinical trial of weekly and daily treatment with camptothecin (NSC-100880): correlation with preclinical studies. Cancer Chemother Rep 56: 515–521, 1972

Slichenmyer WJ, Rowinsky EK, Donehower RC, And Kaufmann SH. The current status of camptothecin analogues as antitumor agents. J Natl Cancer Inst 85: 271–291, 1993.

Wall ME, Wani MC, Cook CE, et al. Plant anti-tumor agents. 1. The isolation and structure of camptothecin, a novel alkaloid leukemia and tumor inhibitor from Camptotheca acuminata. J Amer Chem Soc 88:3888–3890, 1966

What is claimed is:

1. A complex comprising a topoisomerase I inhibitor complexed to a phospholipid, the phospholipid comprising two fatty acids attached to a head group, wherein at least one of the fatty acids is an oleic acid.

2. The complex of claim 1, wherein the phospholipid DO-NGPE,DOPG,DOPE,DOPC,DOTMA,DOTAP, or DOPS.

3. The complex of claim 1, wherein the composition is further defined as comprising two phospholipids, each phospholipid comprising two fatty acids attached to a head group wherein at least of the fatty acids in each phospholipid is an oleic acid.

4. The complex of claim 1, further defined as comprising three phospholipids, each phospholipid two fatty acids attached to a head group, wherein at least one of the fatty acids in each phospholipid is an acid.

5. The complex of claim 4 wherein the three phospholipids are DOPE, DOPC, and DOTAP.

6. The complex of claim 5, wherein the DOPE, DOPC, and DOTAP are in a ratio of 40%:40%:20%.

7. The complex of claim 1, further comprising a positively charged phospholipid.

8. The complex of claim 1, wherein the positively charged phospholipid is DOTAP or stearylamine.

9. The complex of claim 1, further defined as a liposome.

10. The complex of claim 1, further defined as a micelle.

11. The complex of claim 1, wherein the topoisomerase I inhibitor is camptothecin.

12. The complex of claim 1, wherein the topoisomerase I inhibitor is topotecan.

13. The complex of claim 1, wherein the topoisomerase I inhibitor is CPT-11.

14. The complex of claim 1, wherein the topoisomerase I inhibitor is 9 amino camptothecin.

15. The complex of claim 1, wherein the topoisomerase I inhibitor is 9 nitro camptothecin.

16. The complex of claim 1 where the ratio of lipid to topoisomerase I inhibitor is less than 100: 1.

17. The complex of claim 16 where the ratio of lipid to topoisomerase I inhibitor is between 5:1 and 100:1.

18. The complex of claim 17 where the ratio of lipid to topoisomerase I inhibitor is between 10:1 and 25:1.

19. A pharmaceutical composition comprising a pharmaceutically effective amount of an LC-TII comprising a topoisomerase I inhibitor complexed to a phospholipid, the phospholipid comprising two fatty acids attached to a head group, wherein at least one of the fatty acids is an oleic acid wherein the LC-TII is in a pharmaceutically acceptable carrier.

20. The pharmaceutical composition of claim 19, wherein the phospholipid comprising the oleic fatty acid is DOPG, DOPE, DOPC, DOTMA, DOTAP, or DOPS.

21. The pharmaceutical composition of claim 19, comprising the phospholipids DOPE, DOPC, and DOTAP.

22. The pharmaceutical composition of claim 19, comprising a positively charged phospholipid.

23. The pharmaceutical composition of claim 22, wherein the positively charged phospholipid is DOTAP or stearylamine.

24. The pharmaceutical composition of claim 19, wherein the topoisomerase I inhibitor is camptothecin.

25. A phospholipid-topoisomerase I inhibitor complex comprising a topoisomerase I inhibitor complexed to a phospholipid comprising two fatty acids attached to a head group, wherein at least one of the fatty acids is an oleic acid, the phospholipid selected from the group consisting of DO-NGPE, DOPG, DOPE, DOPC, DOTMA, DOTAP and DOPS.

26. The complex of claim 25, wherein the complex is further defined as comprising two phospholipids, each phospholipid comprising two fatty acids attached to a head group, wherein at least one of the fatty acids in each phospholipid is an oleic acid.

27. The complex of claim 26, further defined as comprising three phospholipids, each phospholipid comprising two fatty acids attached to a head group, wherein at least one of the fatty acids in each phospholipid is an oleic acid.

28. The complex of claim 27, wherein the three phospholipids are DOPE, DOPC, and DOTAP.

29. The complex of claim 25, wherein the topoisomerase I inhibitor is camptothecin.

* * * * *

UNITED STATES PATENT AND TRADEMARK OFFICE
CERTIFICATE OF CORRECTION

PATENT NO.    :    5,834,012

DATED         :    November 10, 1998

INVENTOR(S)   :    Perez-Soler, et al.

It is certified that error appears in the above-identified patent and that said Letters Patent is hereby corrected as shown below:

In claim 3, column 22, line 28, after 'group', insert --,--.
In claim 4, column 22, line 34, after 'an', insert --oleic--.
In claim 20, column 23, line 2, after 'oleic', delete --fatty--..

Signed and Sealed this

Ninth Day of March, 1999

Attest:

Q. TODD DICKINSON

Attesting Officer

Acting Commissioner of Patents and Trademarks